(12) United States Patent
Pang et al.

(10) Patent No.: US 8,231,608 B2
(45) Date of Patent: *Jul. 31, 2012

(54) DRUG-DELIVERY PUMPS AND METHODS OF MANUFACTURE

(75) Inventors: Changlin Pang, Pasadena, CA (US); Fukang Jiang, Pasadena, CA (US); Jason Shih, Yorba Linda, CA (US); Sean Caffey, Manhattan Beach, CA (US); Mark Humayun, Glendale, CA (US); Yu-Chong Tai, Pasedena, CA (US)

(73) Assignee: MiniPumps, LLC, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,251

(22) Filed: May 8, 2009

(65) Prior Publication Data

US 2009/0312742 A1   Dec. 17, 2009

Related U.S. Application Data

(60) Provisional application No. 61/051,422, filed on May 8, 2008, provisional application No. 61/197,817, filed on Oct. 30, 2008, provisional application No. 61/197,750, filed on Oct. 30, 2008, provisional application No. 61/201,197, filed on Dec. 8, 2008, provisional application No. 61/198,144, filed on Nov. 3, 2008, provisional application No. 61/150,515, filed on Feb. 6, 2009.

(51) Int. Cl.
*A61K 9/22* (2006.01)
*A61M 5/142* (2006.01)

(52) U.S. Cl. ............ 604/891.1; 604/500; 604/132

(58) Field of Classification Search ........... 604/500, 604/132, 891.1, 892.1, 141
See application file for complete search history.

(56) References Cited

U.S. PATENT DOCUMENTS

| | | | |
|---|---|---|---|
| 3,894,538 A * | 7/1975 | Richter | 604/891.1 |
| 3,916,899 A | 11/1975 | Theeuwes et al. | |
| 3,977,404 A | 8/1976 | Theeuwes | |
| 4,164,560 A | 8/1979 | Folkman et al. | |
| 4,543,088 A | 9/1985 | Bootman et al. | |
| 4,553,973 A | 11/1985 | Edgren | |
| 4,738,657 A | 4/1988 | Hancock et al. | |

(Continued)

FOREIGN PATENT DOCUMENTS

DE       3915708       2/1990

(Continued)

OTHER PUBLICATIONS

Invitation to Pay Additional Fees and Partial International Search for PCT Application No. PCT/US2009/043317, mailed Nov. 16, 2009, 5 pages.

(Continued)

*Primary Examiner* — Jackie Ho
*Assistant Examiner* — Michael J Anderson
(74) *Attorney, Agent, or Firm* — Bingham McCutchen LLP

(57) ABSTRACT

Embodiments of an implantable electrolytic pump include a first expandable diaphragm and a second flexible diaphragm, and first and second chambers each for containing a fluid, wherein the first expandable diaphragm separates the first and second chambers and provides a fluid barrier therebetween, and the second chamber is formed between the first expandable diaphragm and the second flexible diaphragms. The pump may further include electrolysis electrodes within the first chamber for causing generation of a gas therein and to thereby expand the expandable diaphragm so that fluid is forced from the second chamber into a cannula.

50 Claims, 26 Drawing Sheets

U.S. PATENT DOCUMENTS

| | | | |
|---|---|---|---|
| 4,751,926 A | 6/1988 | Sasaki | |
| 4,760,837 A | 8/1988 | Petit | |
| 4,781,675 A | 11/1988 | White | |
| 4,781,695 A | 11/1988 | Dalton | |
| 4,838,887 A | 6/1989 | Idriss | |
| 4,853,224 A | 8/1989 | Wong | |
| 4,888,176 A | 12/1989 | Langer et al. | |
| 4,959,217 A | 9/1990 | Sanders et al. | |
| 5,135,499 A | 8/1992 | Tafani et al. | |
| 5,147,647 A | 9/1992 | Darougar et al. | |
| 5,164,188 A | 11/1992 | Wong | |
| 5,171,213 A | 12/1992 | Price, Jr. | |
| 5,178,604 A | 1/1993 | Baerveldt et al. | |
| 5,252,192 A | 10/1993 | Ludwig | |
| 5,318,540 A * | 6/1994 | Athayde et al. | 604/141 |
| 5,407,441 A | 4/1995 | Greenbaum | |
| 5,443,505 A | 8/1995 | Wong et al. | |
| 5,462,739 A | 10/1995 | Dan et al. | |
| 5,472,436 A | 12/1995 | Fremstad | |
| 5,476,445 A | 12/1995 | Baerveldt et al. | |
| 5,704,520 A | 1/1998 | Gross et al. | |
| 5,725,017 A | 3/1998 | Elsberry et al. | |
| 5,725,493 A | 3/1998 | Avery et al. | |
| 5,798,115 A | 8/1998 | Santerre et al. | |
| 5,824,072 A | 10/1998 | Wong | |
| 5,830,173 A | 11/1998 | Avery et al. | |
| 5,836,935 A | 11/1998 | Ashton et al. | |
| 5,868,697 A | 2/1999 | Richter et al. | |
| 5,904,144 A | 5/1999 | Hammang et al. | |
| 5,989,579 A | 11/1999 | Darougar et al. | |
| 6,144,106 A * | 11/2000 | Bearinger et al. | 257/789 |
| 6,251,090 B1 | 6/2001 | Avery et al. | |
| 6,264,971 B1 | 7/2001 | Darougar et al. | |
| 6,281,192 B1 | 8/2001 | Leahy et al. | |
| 6,375,972 B1 | 4/2002 | Guo et al. | |
| 6,416,777 B1 | 7/2002 | Yaacobi | |
| 6,520,936 B1 | 2/2003 | Mann | |
| 6,669,950 B2 | 12/2003 | Yaacobi | |
| 6,713,081 B2 | 3/2004 | Robinson et al. | |
| 6,719,750 B2 | 4/2004 | Varner et al. | |
| 6,852,106 B2 | 2/2005 | Watson et al. | |
| 7,070,577 B1 | 7/2006 | Haller et al. | |
| 7,276,050 B2 | 10/2007 | Franklin | |
| 2002/0103412 A1 | 8/2002 | Trimmer | |
| 2002/0188282 A1 | 12/2002 | Greenberg | |
| 2003/0014036 A1 | 1/2003 | Varner et al. | |
| 2003/0064088 A1 | 4/2003 | Carvalho et al. | |
| 2003/0069560 A1 | 4/2003 | Adamis et al. | |
| 2003/0141618 A1 | 7/2003 | Braithwaite et al. | |
| 2004/0028655 A1 | 2/2004 | Nelson et al. | |
| 2004/0106914 A1* | 6/2004 | Coppeta et al. | 604/892.1 |
| 2004/0143221 A1 | 7/2004 | Shadduck | |
| 2004/0199130 A1 | 10/2004 | Chornenky et al. | |
| 2005/0175708 A1 | 8/2005 | Carrasquillo et al. | |
| 2005/0187515 A1 | 8/2005 | Varrichio et al. | |
| 2005/0208103 A1 | 9/2005 | Adamis et al. | |
| 2006/0116641 A1* | 6/2006 | Gordon et al. | 604/141 |
| 2006/0167435 A1 | 7/2006 | Adamis et al. | |
| 2006/0258994 A1 | 11/2006 | Avery | |
| 2006/0259015 A1 | 11/2006 | Steinbach | |
| 2007/0021735 A1* | 1/2007 | Bhavaraju et al. | 604/891.1 |
| 2007/0112328 A1 | 5/2007 | Steinbach et al. | |
| 2007/0255235 A1 | 11/2007 | Olsen et al. | |
| 2007/0255261 A1 | 11/2007 | Haase | |
| 2008/0039792 A1 | 2/2008 | Meng et al. | |
| 2009/0281528 A1* | 11/2009 | Grovender et al. | 604/892.1 |

FOREIGN PATENT DOCUMENTS

| | | |
|---|---|---|
| EP | 0251680 | 1/1988 |
| GB | 1345764 | 2/1974 |
| IE | 38474 | 3/1978 |
| WO | WO-95/13838 A1 | 5/1995 |
| WO | WO-99/17749 | 4/1999 |
| WO | WO-99/38552 | 8/1999 |
| WO | WO-99/62576 | 12/1999 |
| WO | WO-00/26367 | 5/2000 |
| WO | WO-00/40089 | 7/2000 |
| WO | WO-01/12158 | 2/2001 |
| WO | WO-01/56634 | 8/2001 |
| WO | WO-01/66173 | 9/2001 |
| WO | WO-01/94784 A1 | 12/2001 |
| WO | WO-03/002170 | 1/2003 |
| WO | WO-03/024360 | 3/2003 |
| WO | WO-2004/014969 | 2/2004 |
| WO | WO-2004/066871 | 8/2004 |
| WO | WO-2004/073551 | 9/2004 |
| WO | WO-2005/046769 | 5/2005 |
| WO | WO-2006/012280 | 2/2006 |
| WO | WO-2006/014793 | 2/2006 |
| WO | WO-2006/075016 | 7/2006 |
| WO | WO-2007/084765 | 7/2007 |
| WO | WO-2007/106557 | 9/2007 |

OTHER PUBLICATIONS

Invitation to Pay Additional Fees and Partial International Search for PCT Application No. PCT/US2009/043313, mailed Nov. 16, 2009, 6 pages.

International Search Report for PCT Application No. PCT/US2009/043325, mailed Dec. 11, 2009, 9 pages.

Written Opinion for PCT Application No. PCT/US2009/043325, mailed Dec. 11, 2009, 9 pages.

Examination Report for European Patent Application No. 07753177.0, mailed Feb. 5, 2010, 3 pages.

International Search Report for PCT Application No. PCT/US2009/043317, mailed Feb. 16, 2010, 7 pages.

Written Opinion for PCT Application No. PCT/US2009/043317, mailed Feb. 16, 2010, 8 pages.

International Search Report for PCT Application No. PCT/US2009/043313, mailed Feb. 25, 2010, 8 pages.

Written Opinion for PCT Application No. PCT/US2009/043313, mailed Feb. 25, 2010, 8 pages.

"FDA Approves and Industry FIRST!—The MED-EL Cochlear Implant System in FDA Approved for Use With Magnetic Resonance Imaging (MRI)," PR Newswire, Durham, N.C., Jun. 18, 2003, 3 pages.

"Krupin Eye Valve with Scleral Buckle, Krupin Eye Valve With Disk," Hood Laboratories Catalogue, F 079 Rev. Nov. 1992, 4 pages.

"The Optimed Advantage—Glaucoma Pressure Regulator," Optimed Advertising Brochure, Journal of Glaucoma, vol. 2, No. 3, 1993, 4 pages.

Chen et al. "Floating-Disk Parylene Micro Check Valve," Micro Electro Mechanical Systems, 2007, IEEE 20th International Conference on MEMS, Jan. 21-25, 2007, 4 pages.

Chen et al. "Floating-Disk Parylene Microvalve for Self-Regulating Biomedical Flow Controls," IEEE 21st International Conference on MEMS, 2008, Jan. 13-17, 2008, 4 pages.

Chen et al. "Surface-Micromachined Parylene Dual Valves for On-Chip Unpowered Microflow Regulation," Journal of Microelectromechanical Systems, vol. 16, No. 2, Apr. 2007, pp. 223-231.

Choudhri et al. "A Comparison of Dorzolamide-Timolol Combination Versus the Concomitant Drugs," American Journal of Ophthalmology, Dec. 2000, 130, pp. 832-833.

Eliason et al. "An Ocular Perfusion System," Invest. Ophthalmol. Vis. Sci., vol. 19, No. 1, Jan. 1980, pp. 102-105.

Hashizoe et al. "Scleral Plug of Biodegradable Polymers for Controlled Release in the Vitreous" Arch Ophthalmol, vol. 112, Oct. 1994, pp. 1380-1384.

Jabs "Treatment of Cytomegalovirus Retinitis—1992," Arch Ophthlmol, vol. 110, Feb. 1992, pp. 185-187.

Khouri et al. "Use of Fixed-Dose Combination Drugs for the Treatment of Glaucoma," Drugs Aging, 2007, 24, 12, pp. 1007-1016.

Kimura et al. "A New Vitreal Drug Delivery System Using an Implantable Biodegradable Polymeric Device," Investigative Ophthalmology & Visual Science, May 1994, vol. 35, No. 6; pp. 2815-2819.

Lo et al. "A Refillable Polymer Drug Delivery Device for Treatment of Ocular Diseases," The Royal Society of Chemistry, Jan. 1, 2007, 28 pages.

Michelson et al. "Experimental Endophtalmitis Treated With an Implantable Osmotic Minipump," Arch Ophthalmol, vol. 97, Jul. 1979, pp. 1345-1346.

Miki, et al. "A Method for Chronic Drug Infusion Into the Eye," Japanese Journal of Ophthalmology, vol. 28, 1984, pp. 140-146.

Pincus et al. "Why are Only 50% of Courses of Anti-Tumor Necrosis Factor Agents Continued for Only 2 Years in Some Settings? Need for Longterm Observations in Standard Care to Compliment Clinical Trials," Journal of Rheumatology, 2006, 33, 12, pp. 2372-2375.

Pope et al. "MRI in Patients with High-Grade Gliomas Treated with Bevacizumab and Chemotherapy," Neurology, 2006, 66, pp. 1258-1260.

Rubsamen et al. "Prevention of Experimental Proliferative Vitreoretinopathy With a Biodegradable Intravitreal Implant for the Sustained Release of Fluorouracil," Arch Ophthalmol, vol. 112, Mar. 1994, pp. 407-413.

Sanborn et al. "Sustained-Release Ganciclovir Therapy for Treatment of Cytomegalovirus Retinitis," Arch Ophthmol, vol. 110, Feb. 1992; pp. 188-195.

Smith et al. "Intravitreal Sustained-Release Ganciclovir," Arch Ophthlmol, vol. 110, Feb. 1992, pp. 255-258.

Stark-Vance, "Bevacizumab and CPT-11 in the Treatment of Relapsed Malignant Glioma," Abstract from the World Federation of Neuro-Oncology Second Quadrennial Meeting and Sixth Meeting of the European Association for Neuro-Oncology, May 5-8, 2005, Abstract 342, p. 369.

Steyer "Alcon Eye-Drug Setback Raises the Stakes," The Street. Com, Oct. 14, 2004, 4 pages.

Strohmaier et al. "The Efficacy and Safety of the Dorzolamide-Timolol Combination Versus the Concomitant Administration of its Components," Ophthalmology, Oct. 1998, vol. 105, No. 10, pp. 1936-1944.

Examination Report for European Patent Application No. 07753177.0, mailed Jan. 29, 2009, 6 pages.

Invitation to Pay Additional Fees and Partial International Search for PCT Application No. PCT/US2007/006530, mailed Jul. 31, 2007, 7 pages.

International Search Report for PCT Application No. PCT/US2007/006530, mailed Nov. 12, 2007, 7 pages.

Written Opinion for PCT Application No. PCT/US2007/006530, mailed Nov. 12, 2007, 10 pages.

Invitation to Pay Additional Fees and Partial International Search for PCT Application No. PCT/US2009/030019, mailed Jun. 5, 2009, 5 pages.

International Search Report for PCT Application No. PCT/US2009/030019, mailed Jul. 20, 2009, 7 pages.

Written Opinion for PCT Application No. PCT/US2009/030019, mailed Jul. 20, 2009, 9 pages.

Invitation to Pay Additional Fees and Partial International Search for PCT Application No. PCT/US2008/087690, mailed May 15, 2009, 5 pages.

International Search Report for PCT Application No. PCT/US2008/087690, mailed Aug. 11, 2009, 7 pages.

Written Opinion for PCT Application No. PCT/US2008/087690, mailed Aug. 11, 2009, 10 pages.

\* cited by examiner

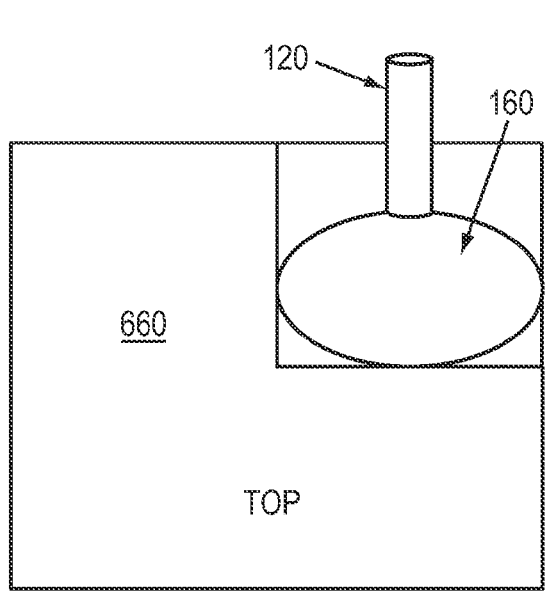
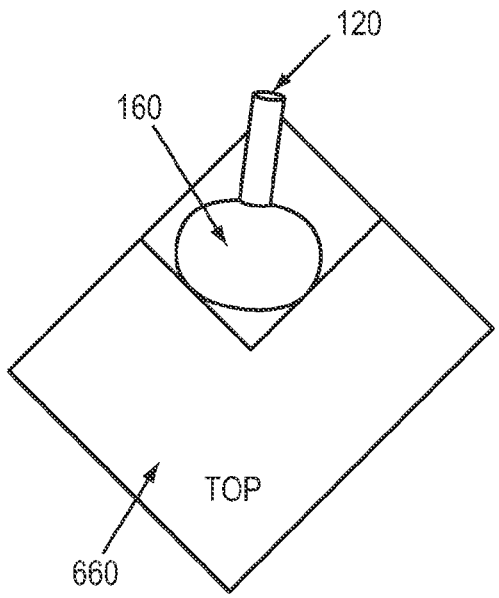
FIG. 20  FIG. 21
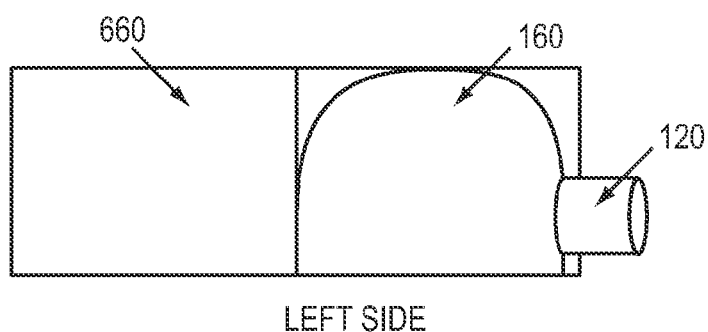
FIG. 22
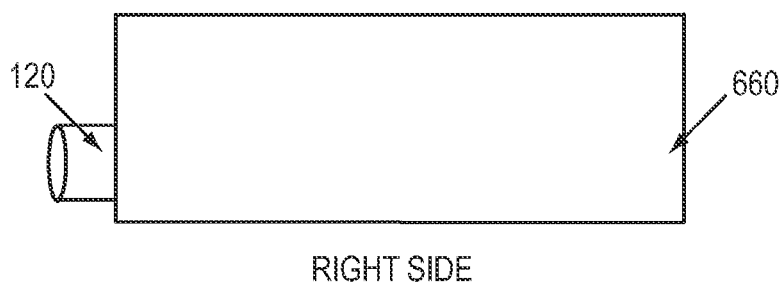
FIG. 23

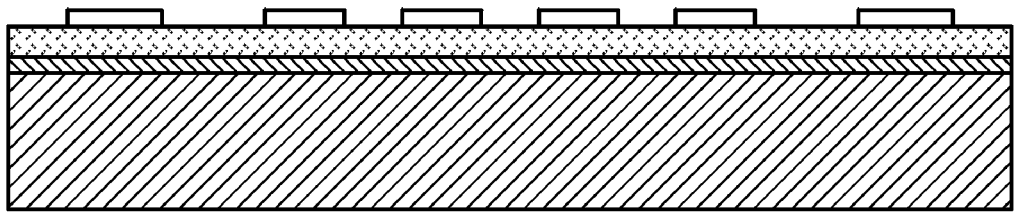
1. COAT PHOTORESIST, PARYLENE AND PLATINUM ON Si WAFER. PATTERN PLATINUM.
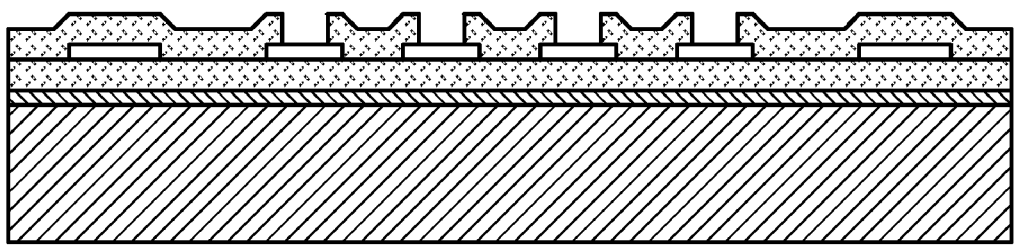
2. DEPOSIT AND PATTERN 2$^{ND}$ PARYLENE LAYER.
3. CUT AND RELEASE FILM. ETCH BACKSIDE PARYLENE TO OPEN CONTACTS USING A SHADOW MASK. ANNEALING AT 200°C IN VACUUM OVEN FOR 10 hrs.
FIG. 37

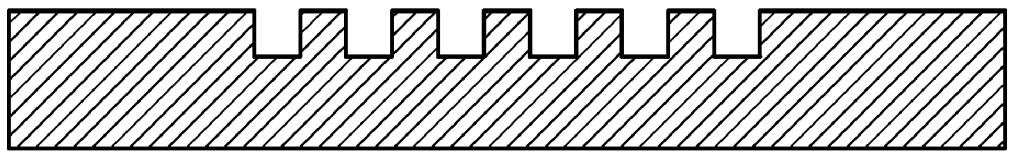
1. PATTERN BARE Si WAFER IN DRIE.
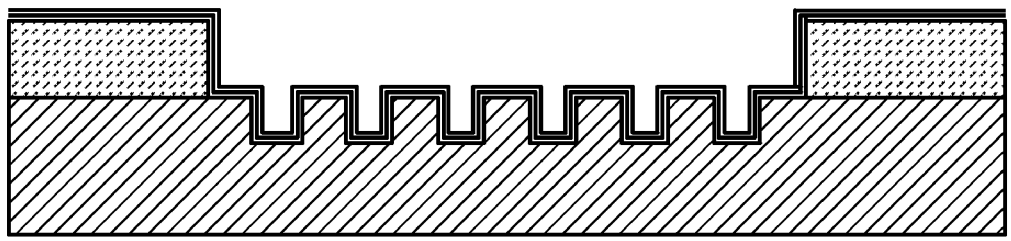
2. COAT AND PATTERN 0.4 mm THICK SU-8 RESIST.
SPRAY COAT REGULAR PHOTORESIST. DEPOSIT 10 um THICK PARYLENE.
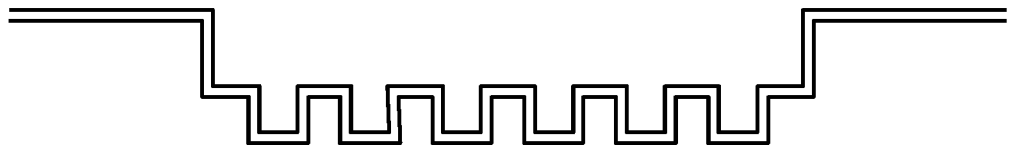
3. IF NECESSARY, DEPOSIT PLATINUM USING A SHADOW MASK
TO COVER THE FLAT AREAS ON THE LEFT AND RIGHT.
CUT AND RELEASE THE DIAPHRAGM.
FIG. 38

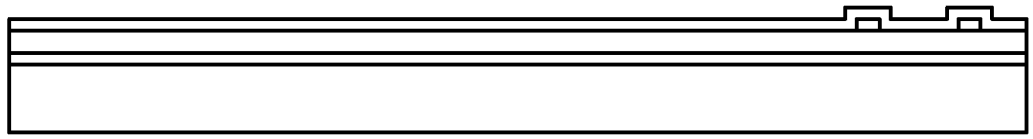

1. COAT PHOTORESIST AND PARYLENE.
DEPOSIT AND PATTERN PLATINUM. COAT 2$^{ND}$ LAYER OF PARYLENE.

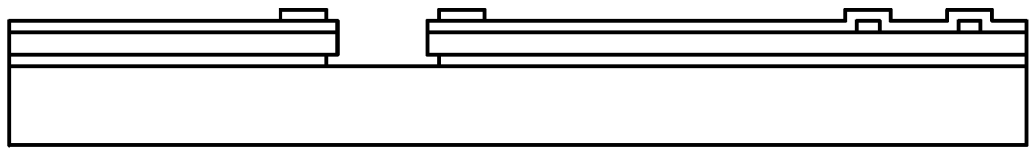

2. DEPOSIT AND PATTERN Ti/Au.
PATTERN PARYLENE TO OPEN THE INLET. COAT SAM LAYER.

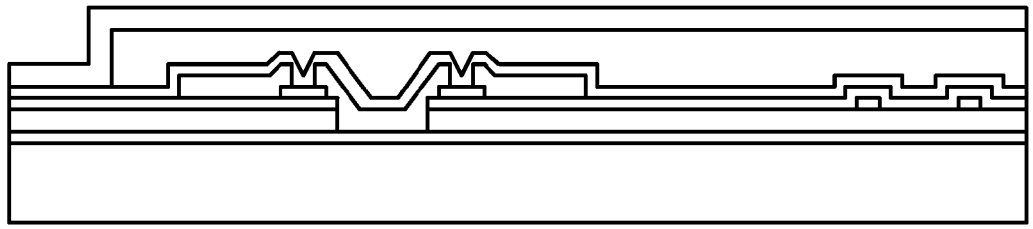

3. COAT AND PATTERN PHOTORESIST. DEPOSIT AND PATTERN
3$^{RD}$ PARYLENE LAYER. COAT AND PATTERN PHOTORESIST.
DEPOSIT AND PATTERN 4$^{TH}$ PARYLENE LAYER.

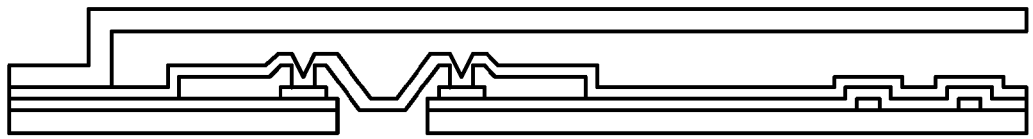

4. RELEASE THE CANNULA.
OPEN BACKSIDE CONTACTS USING A SHADOW MASK.

FIG. 39

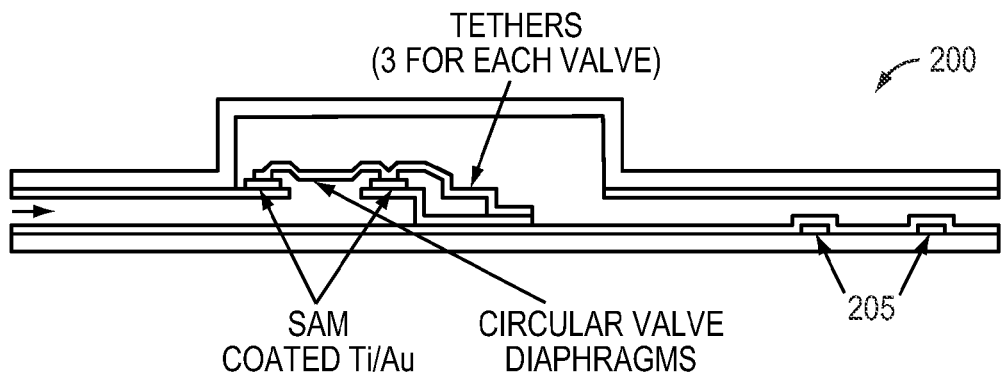

FIG. 40

DRUG-DELIVERY PUMPS AND METHODS OF MANUFACTURE

CROSS-REFERENCE TO RELATED APPLICATIONS

This application claims priority to, and the benefit of, U.S. Provisional Patent Application Nos. 61/051,422, filed on May 8, 2008; 61/197,817, filed on Oct. 30, 2008; 61/197,750, filed on Oct. 30, 2008; 61/201,197, filed on Dec. 8, 2008; 61/198,144, filed on Nov. 3, 2008; and 61/150,515, filed on Feb. 6, 2009, the entire disclosures of which are hereby incorporated herein by reference.

TECHNICAL FIELD

In various embodiments, the invention relates to the delivery of therapeutic fluids, and more particularly to implantable systems and methods for delivering therapeutic fluids to a treatment site within a body.

BACKGROUND

Medical treatment often requires the administration of a therapeutic agent (e.g., medicament, drugs, etc.) to a particular part of a patient's body. As patients live longer and are diagnosed with chronic and/or debilitating ailments, the likely result will be an increased need to place even more protein therapeutics, small-molecule drugs, and other medications into targeted areas throughout the patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted (and generally offer limited ability to change the dose in response to the clinical picture).

Another example is cancer, such as breast cancer or meningiomas, where large doses of highly toxic chemotherapies, such as rapamycin, bevacizumab (e.g., Avastin), or irinotecan (CPT-11), are typically administered to the patient intravenously, which may result in numerous undesired side effects outside the targeted area. Other examples of difficult-to-reach anatomical regions for drug delivery include the knee, where drugs often have difficulty penetrating the avascular cartilage tissue for diseases such as osteoarthritis, the brain, and the spine.

Methods that use an implantable drug delivery system, which may include a refillable drug reservoir, a cannula for delivering the drug, etc., generally allow for controlled delivery of pharmaceutical solutions to a specified target. This approach can minimize the surgical incision needed for implantation and typically avoids future or repeated invasive surgery or procedures. In ocular applications, implantable devices sometimes utilize a passive mechanism for drug delivery, in which drug is pumped out when, for example, a finger is pressed on the drug reservoir. This may, however, render the control of the administered drug dosage problematic. In addition, the fabrication of such devices may require cumbersome and expensive hand-assembling work. Electrolysis-driven implantable MEMS drug-delivery devices are also known, but may be rigid and therefore risk damage to the site of implantation (particularly where delicate (e.g., ocular) tissue is involved).

A need exists, therefore, for improved implantable drug-delivery devices and methods of manufacture.

SUMMARY OF THE INVENTION

In various embodiments, the present invention relates to improved systems and methods for delivering a drug to a target location within a body, and methods of manufacturing systems for drug delivery. Pumps in accordance with the invention may be shaped to conform to a particular anatomical region, and may be sized for any of a variety of anatomical sites. They can be made of biocompatible materials (e.g., parylene) to enhance patient comfort and safety.

Some embodiments of the invention relate to electrolytic pumps and, in particular, designs and features that relieve pressure buildup during operation, thereby avoiding needless power loss and long actuation times. Particular implementations can include, for example, osmotic membranes or perforated shells; indeed, an osmotic mechanism can be used to drive pump operation instead of (or in addition to) relieving internal pressure.

Some embodiments of the invention relate to data telemetry and wireless powering and programming of an implanted pump, and to particular operative and control components that extend device capabilities. For example, external communication with (and/or wireless recharging of) an internally implanted pump may take place using a wearable telemetry and/or charging device implemented, for example, in eyeglasses or an eye patch for the eye, a headband for the brain or a kneebrace for the knee; when the user wears the device as intended, optimal alignment between communicating components may be enforced. Telemetry may be electromagnetic or, in some implementations, optical.

Some embodiments of the invention relate to efficient powering of an implantable pump, and the use of redundant power sources for safety purposes. For example, a redundant battery may take over pump operation upon failure of the main battery, or may instead execute a controlled shutdown of the pump and/or issuance of an alert. The alert may include an audible signal, a vibration, an optical signal, a shock, and/or a transcutaneous neural stimulation.

Some embodiments of the invention relate to convenient, automated manufacture of implantable pumps as described herein. Embodiments of the invention also facilitate convenient sterilization of implantable pumps without damage to vulnerable components thereof.

Accordingly, one aspect of the invention pertains to an implantable electrolytic pump, embodiments of which include a first expandable diaphragm and a second flexible diaphragm and first and second chambers each for containing a fluid. The first expandable diaphragm separates the first and second chambers and provides a fluid barrier therebetween, and the second chamber is formed between the first expandable diaphragm and the second flexible diaphragm. The pump further includes a perforated shell over the second flexible diaphragm, a cannula for conducting liquid from the second chamber, and electrolysis electrodes within the first chamber for causing generation of a gas (e.g. electrolysis) therein and to thereby expand the expandable diaphragm so that fluid is forced from the second chamber into the cannula, whereby body fluid is admitted through the shell perforations to relieve vacuum pressure on the second chamber. At least one of the diaphragms may include or consist essentially of parylene and/or a composite material (e.g. a parylene-metal-parylene combination including platinum and parylene).

In one embodiment, the perforated shell is substantially rigid and/or includes at least one of a biocompatible plastic material or a metal. The perforated shell may have a thickness of greater than 0.1 mm. The pump may include a casing, which may be formed, at least in part, by the perforated shell, or be a separate element. The casing may include or consist essentially of a material selected from the group consisting of a ceramic, an epoxy encapsulation, a metal (e.g., titanium (Ti), niobium (Nb), tantalum (Ta)), polyetheretherketone (PEEK), polypropylene, polydimethylsiloxane (PDMS), and parylene. The casing may be at least partially coated with parylene. The perforated shell may include one or more perforations for allowing a body fluid to flow therethrough, with the perforations sized and shaped to allow a body fluid to flow therethrough at a sufficient rate to substantially offset a vacuum pressure applied to the second flexible diaphragm.

The pump may include additional features including, but not limited to, at least one refill port, a check valve, a sensor (e.g. a pressure, chemical, and/or flow sensor), and/or circuitry, disposed below the first chamber and electrically connected to the electrodes, for operating the electrodes. The check valve prevents leakage of a fluid from the second chamber when the pump is at rest or during a refilling process and/or prevents backward fluid flow through the cannula and into the second chamber. At least one of the check valve, pressure sensor, chemical sensor, and/or flow sensor may be located within the cannula. The circuitry can be used, for example, to adjustably control a flow rate from the second chamber. The circuitry may include a data storage means, a data transmission means such as, but not limited to, a wireless telemetry circuit, and/or a data receiving means. The circuitry may be secured to the electrodes by a conductive epoxy which may include or consists essentially of a biocompatible material (e.g., gold or silver). The circuitry may provide an adjustable current or voltage to the electrolysis electrodes to adjustably control the flow rate from the second chamber. The electrolysis electrodes may include, or consist essentially of, for example, platinum, gold, or silver on parylene, ceramic, and/or a biocompatible insulator. In one embodiment, the first chamber comprises a recombination catalyst, e.g., platinum. At least one of the expandable membranes may include corrugations and/or bellows folds.

The first chamber may contain at least one fluid that undergoes at least a partial phase change from a liquid state to a gaseous state (or, more generally, evolves gas) upon activation of the electrolysis electrodes, with the fluid returning from a gaseous state to a liquid state upon deactivation of the electrolysis electrodes, e.g. in the presence of a catalyst. The fluid(s) may include, or consist essentially of, a saline solution, a solution comprising magnesium sulfate, a solution comprising sodium sulfate, pure water, or any non-toxic solution.

In one embodiment, the pump includes an osmotic diaphragm between the second flexible diaphragm and the perforated shell. In one embodiment, the perforated shell forms the osmotic diaphragm. A third chamber is formed between the second flexible diaphragm and the osmotic diaphragm. The osmotic diaphragm may be at least partially anchored to the perforated shell. The third chamber may contain an osmosis chamber fluid such as at least one solvent and at least one solute, and may include a fluid such as, but not limited to, a saline solution, a solution comprising magnesium sulfate, or a solution comprising sodium sulfate. A refill port may be positioned in fluid communication with the third chamber. In operation, the osmotic diaphragm allows a surrounding body fluid to flow into the third chamber at a sufficient rate to substantially offset a pressure applied to the second flexible diaphragm.

The pump may include a plurality of first chambers and/or a plurality of second chambers. The pump may also include refill ports in communication with one or more of the chambers. At least one cannula may be placed in fluid communication with one or more of the plurality of second chambers. Each of the first chambers may include separately controllable electrolysis electrodes. In one embodiment, a plurality of cannulas are placed in fluid communication with a single second chamber.

Another aspect of the invention relates to a method of administering a drug. The method includes providing a pump comprising an electrolysis chamber, a drug chamber and a perforated shell thereover, the shell being in contact with a surrounding fluid, and activating the electrolysis chamber to dispense a volume of drug from the drug chamber. The drug chamber decreases in volume following drug dispensation, and fluid is admitted through the shell perforations to offset the decreased volume of the drug chamber and prevent buildup of vacuum pressure thereon. In one embodiment, the activating step includes activating electrolysis electrodes within the electrolysis chamber for causing generation of a gas (e.g. electrolysis) therein. The electrolysis chamber may contain at least one liquid electrolyte which causes electrolysis of the gas. The gas may thereafter return to a substantially liquid state upon deactivation of the electrolysis electrodes. The fluid may include, or consist essentially of, a saline solution, a solution comprising magnesium sulfate, a solution comprising sodium sulfate, pure water, or any non-toxic solution. The electrolysis chamber may include a recombination catalyst (e.g. platinum) to help catalyze the gas back into a liquid.

In operation, the generation of a gas (e.g. electrolysis) within the electrolysis chamber expands a first expandable diaphragm located between the electrolysis chamber and the drug chamber. The pump may further include a second flexible diaphragm located between the drug chamber and the perforated shell, with the first and/or second diaphragm including or consisting essentially of parylene and/or a composite material (e.g. a parylene-metal-parylene combination including platinum and parylene).

The perforated shell may be substantially rigid and/or may include at least one of a biocompatible plastic material and/or a metal. The perforations in the perforated shell may be sized and shaped to allow a body fluid to flow therethrough at a sufficient rate to substantially offset a vacuum pressure applied to the drug chamber. The pump may further include an osmotic diaphragm between the drug chamber and the perforated shell to form an osmosis chamber between the drug chamber and the osmotic diaphragm, the osmotic diaphragm allowing a body fluid to flow therethrough into the osmosis chamber. The osmotic diaphragm may allow a body fluid to flow into the third chamber at a sufficient rate to substantially offset the decreased volume of the drug chamber.

In one embodiment, the drug is dispensed through one or more cannulas in fluid communication with the drug chamber. The dispensing of the drug may be controlled by at least one check valve and/or monitored by at least one sensor (e.g. a pressure, a chemical, and/or a flow sensor).

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

These and other objects, along with advantages and features of embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 20 shows a schematic plan view of another shell for a pump, in accordance with one embodiment of the invention;

FIG. 21 is a schematic plan view of the pump of FIG. 20 with the cannula redirected;

FIG. 22 shows a schematic side view of the pump of FIG. 20;

FIG. 23 shows another schematic side view of the pump of FIG. 20;

FIG. 37 shows steps in the fabrication of an electrolysis chamber for a pump in accordance with an embodiment of the invention;

FIG. 38 shows steps in the fabrication of a corrugated diaphragm for a pump in accordance with an embodiment of the invention;

FIG. 39 shows steps in the fabrication of a cannula with integrated check valve and flow sensor in accordance with an embodiment of the invention;

FIG. 40 is a schematic elevation of a modified cannula as fabricated using the process of FIG. 39.

DESCRIPTION

Figure 1:
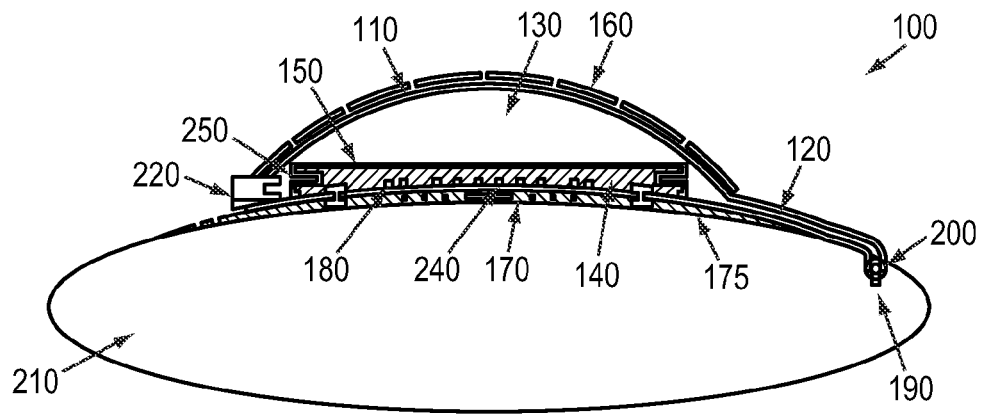
FIG. 1 shows a schematic sectional view of a drug-delivery pump implanted in a patient's eye, in accordance with one embodiment of the invention.

In general, embodiments of the present invention relate to electrolysis-actuated, implantable drug-delivery pumps such as, but not limited to, pumps based on micro-electro-mechanical systems ("MEMS"). Devices in accordance with the invention may, in some embodiments, be monolithically microfabricated on multiple polymer layers. Parylene (a polymer of p-xylene) or other biocompatible materials may be employed to achieve an active device with full biocompatibility. For example, a drug reservoir, electrolysis chamber, cannula, check valve, and/or suture structure of an implantable drug-delivery pump may each be manufactured, at least in part, from parylene. The implantable drug-delivery pump may be used for the delivery of, for example, fluid (e.g., a drug in liquid form), cells, biologics, and/or a suspension of inorganic and/or organic particles into the body of human or animal subjects.

In various embodiments of the invention, components, such as electrolysis electrodes, an application specific integrated circuit ("ASIC") or standard microcontroller chip, a battery, a coil for power reception and two-way data transmission, flow, chemical, and pressure sensors, etc., may be embedded and integrated within the drug-delivery device and, for example, within parylene films incorporated into the device. In one embodiment, the device is flexible and easy to fit into a protective shell having an optimized three-dimensional (3D) implantation geometry.

One or more portions of the implantable pump may be manufactured from a film of biocompatible material such as, but not limited to, parylene (e.g., parylene C). Parylene films may be formed from a pure molecular precursor (a monomer vapor), and generally have no contaminating inclusions, do not "outgas," and form effective barriers against the passage of contaminants to both the patient's body and the surrounding environment. The parylene films may generally be relatively thin and pinhole-free, non-liquid (no meniscus effects), produce no cure forces (applied at room temperature), and contain substantially no additives (catalysts, plasticizers, solvents). Parylene films may also provide a suitable barrier (against moisture, fluids, and gases), be inert (i.e., insoluble in most solvents), lubricious, highly dielectric, biocompatible and biostable, sterilization-tolerant, and compatible with most vacuum-stable materials (such as, but not limited to, silicon, plastics, metals, ceramics, fabrics, paper, and granular materials). In an alternative embodiment, other biocompatible, water-resistant polymers, such as, but not limited to, polydimethylsiloxane (PDMS), polyvinylidene fluoride (PVDF), and/or various piezoelectric polymers, can be used in place of, or in addition to, parylene films. In a further embodiment, biocompatible composite materials (e.g. a parylene-metal-parylene combination including platinum and parylene) may be used in the diaphragm in place of, or in addition to, parylene and/or other biocompatible polymers.

Embodiments of the invention may be used to deliver a measured drug dosage to a treatments site within a number of locations within a body, such as, but not limited to, the eye, the brain, or the knee, Having a drug pump to dose the brain's parenchyma directly, for example, may be helpful in treating diseases such as Parkinson's Disease, Alzheimer's Disease, cancer, stroke recovery and hydrocephalys. In one exemplary embodiment, a pump may be implanted in the sub-arachnoid space of the brain to provide chemotherapy or to provide another type of treatment for the brain, or near a tumor in any portion of the patient's body to provide chemotherapy, or in a pancreas that does not respond well to glucose to provide agents (e.g., proteins, viral vectors, etc.) that will trigger insulin release, or elsewhere. Similarly, using an implantable pump to inject one or more drugs, such as anti-inflammatories (e.g. steroids, S-adenosylmethionine), hyaluronic acid, amino acids (e.g. calcitonin), directly to tissues within the knee, can help treat tissues such as cartilage which is known to have a very poor vascular supply. The pump may also be useful in treating other areas of the body, such as the spine, to deliver pain medications (e.g. fentynl, morphine) and/or anti-inflammatories, where standard therapies have been expensive or ineffective.

An exemplary drug-delivery pump, implanted within a patient's eye, is shown in FIG. 1. In this embodiment, the implantable MEMS drug-delivery pump 100 includes a pair of chambers 130, 140 (e.g., parylene envelopes) and a cannula 120. The top chamber 130 defines a drug reservoir that contains one or more drugs to be administered in liquid form, and the bottom chamber 140 contains a fluid (e.g., and electrolytic fluid) which, when subjected to electrolysis, evolves a gas including one or more gaseous products (e.g. in one embodiment, electrolysis of the fluid within the electrolysis chamber produces two gases, $H_2$ and $O_2$). The two chambers are separated by a diaphragm 150. The diaphragm 150 may be elastic and/or may be corrugated to provide for expansion thereof in response to the phase-change of the fluid within the bottom chamber 140 from a liquid to a gaseous state. The diaphragm 150 may be manufactured from one or more parylene films and/or a composite material. The chambers 130, 140 may be positioned within a shaped protective casing or shell 160 made of a relatively rigid biocompatible material (e.g., medical-grade polypropylene, a metal, and/or a biocompatible plastic). The shell 160 provides a hard surface against which an outer wall 110 of the drug reservoir chamber 130 exerts pressure and which protects the pump from inadvertent external forces. The shell 160 may include a solid, perforated or non-perforated biocompatible material coated in parylene. Control circuitry 170, including, for example, a battery and an induction coil for power and data transmission, are embedded under the bottom chamber 140 (e.g., between the bottom wall 180 of the bottom electrolysis chamber 140 and the floor of the shell 160). In one embodiment, the control circuitry 170 is embedded within a protective encapsulation 175 such as, but not limited to, a silicon and/or parylene encapsulation. The control circuitry 170 provides power to one or more electrolysis electrodes 240 positioned within the bottom chamber 140, and may be secured to the electrolysis electrodes 240 by a material such as, but not limited to, a conductive epoxy including a biocompatible material (e.g. gold or silver). The electrolysis electrodes 240 may be formed on or within a parylene film forming the bottom surface of the electrolysis chamber 140. An adhesion layer (e.g. including or consisting of titanium) may be used to adhere the electrolysis electrodes 240 to a bottom surface of the electrolysis chamber 140. Alternatively, the bottom surface of the electrolysis chamber 140 to which the electrolysis electrodes 240 are coupled, or imbedded within, may include a substrate formed from a material including, but not limited to, alumina, zirconium oxide, and/or sapphire. Activation of these electrolysis electrodes 240 produces a phase change in the electrolytic fluid within the bottom chamber 140 by evolving the fluid from a liquid to a gaseous state (i.e. generating a gas through electrolysis).

The cannula 120 connects the drug chamber 130 with a treatment site 190. A check valve 200, one or more flow sensors (not shown), and/or one or more chemical or pressure sensors (also not shown) may be positioned within the cannula 120 to control and/or monitor the flow of drug from the drug chamber 130, through the cannula 120, and into the treatment site 190. Check valves 200 may, for example, prevent leakage of a drug from the drug chamber 130 when the electrolysis electrodes 240 are not activated and/or during a refilling process and/or prevent backward fluid flow through the cannula into the drug chamber 130. The treatment site may be an eye 210 of a patient, or may be any other target body portion. For example, the pump 100 may be implanted in the sub-arachnoid space of the brain to provide chemotherapy or to provide another type of treatment for the brain, or near a tumor in any portion of the patient's body to provide chemotherapy, or in a pancreas that does not respond well to glucose to provide agents (e.g., proteins, viral vectors, etc.) that will trigger insulin release, or elsewhere.

One or more flow sensors, such as, but not limited to, those based upon thermal effects, time-of-flight, and/or pressure, may be inserted at any position along the length of the cannula 120 to monitor the flow of drug—and thereby enable the measurement of drug volume—through the cannula 120. Alternatively or in addition, a pressure sensor may be integrated at the distal end of the cannula 120 in order to measure pressure at the site of administration 190 (e.g., the intravitreal chamber, shoulder capsule, knee capsule, cerebral ventricals, spinal canal, etc.). Further pressure sensors may be integrated along the cannula 120 or placed elsewhere in the pump 100, such as, but not limited to, within the drug chamber 130 and/or bottom electrolysis chamber 140. Chemical sensors may be used, for example, to monitor one or more chemical compositions within a treatment site (e.g. monitoring the brains cerebral spinal fluid (CSF) for chemicals such as osmolarity, sugar and infection). The sensors may provide enough feedback to the control circuitry 170 to allow the flow of drugs to be metered by a closed-loop control process. For example, increased pressure exerted by the surrounding areas may cause the increased flow of drug from the pump 100 to maintain the closed-loop control.

Figure 2:
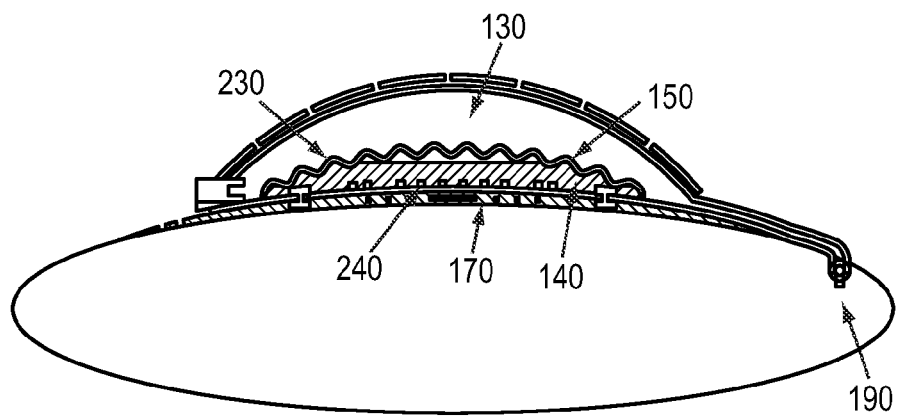
FIG. 2 shows a schematic sectional view of the pump of FIG. 1 with a corrugated membrane.
Figure 3:
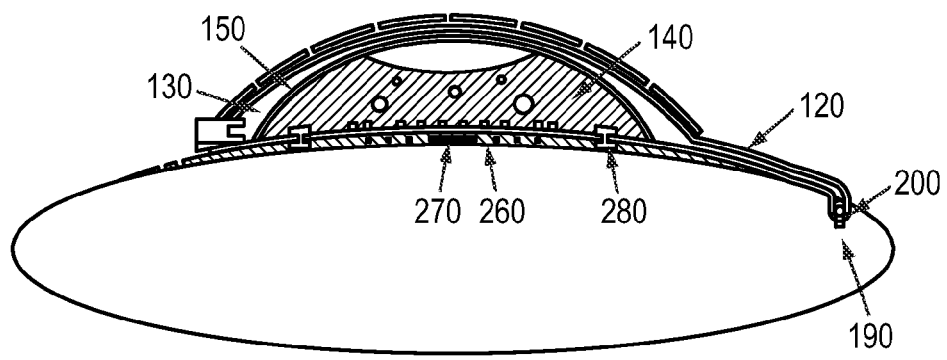
FIG. 3 shows a schematic sectional view of the pump of FIG. 1 with the membrane expanded.

In one embodiment, as illustrated in FIG. 2, the diaphragm 150 includes a plurality of corrugations 230. When current is supplied to the electrolysis electrodes 240 by the circuitry 170, the electrolytic fluid within the bottom chamber 140 evolves into a gas. This phase change increases the volume of the bottom chamber 140, thereby expanding the diaphragm 150, as shown in FIG. 3, and forcing liquid out of the drug reservoir 130, through the cannula 120, and toward the treatment site 190. When current to the electrolysis electrodes 240 is stopped, the gas within the bottom chamber 140 dissipates back into its liquid state, and the diaphragm 150 of the electrolysis chamber recovers its space-efficient corrugations 230. The corrugations 230 permit a large degree of membrane 150 expansion without sacrificing volume within the drug reservoir 130 when the diaphragm 150 is relaxed. In one embodiment, the circuitry 170 provides an adjustable current or voltage to the electrolysis electrodes 240 to adjustably control the expansion of the diaphragm 150 and therefore the flow rate of drug from the drug chamber 130.

In an alternative embodiment, the diaphragm 150 includes a bellows configuration and/or a highly elastic material in addition to, or in place of, the corrugations 230. For example, as shown in FIG. 1, the sidewalls of the membrane 150 have folds 250 forming the bellows structure, so that the membrane 150 is substantially flat in its collapsed configuration. In this embodiment, when the gas is formed in the bottom chamber 140, the folds 250 open and the membrane 150 expands. As a result, the bellows structure 250 may achieve large diaphragm deflections. It should be stressed that essentially any space-saving, expandable arrangement of folds may be utilized. The material of the membrane 150 for any of the embodiments described herein may include, or consist essentially of, parylene and/or other suitable materials.

Figure 4A:
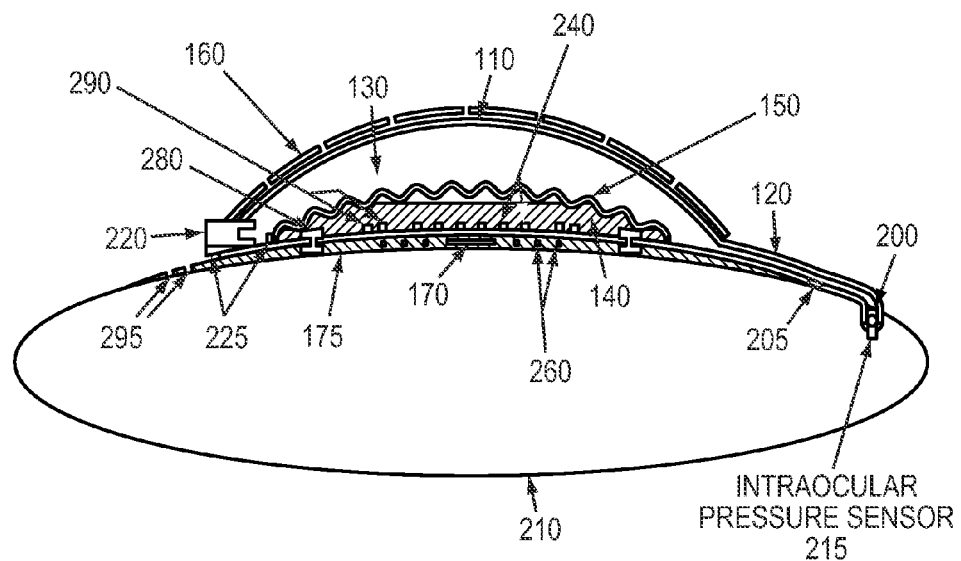
FIG. 4A shows another schematic sectional view of the pump of FIG. 1 implanted in a patient's eye.
Figure 4B:
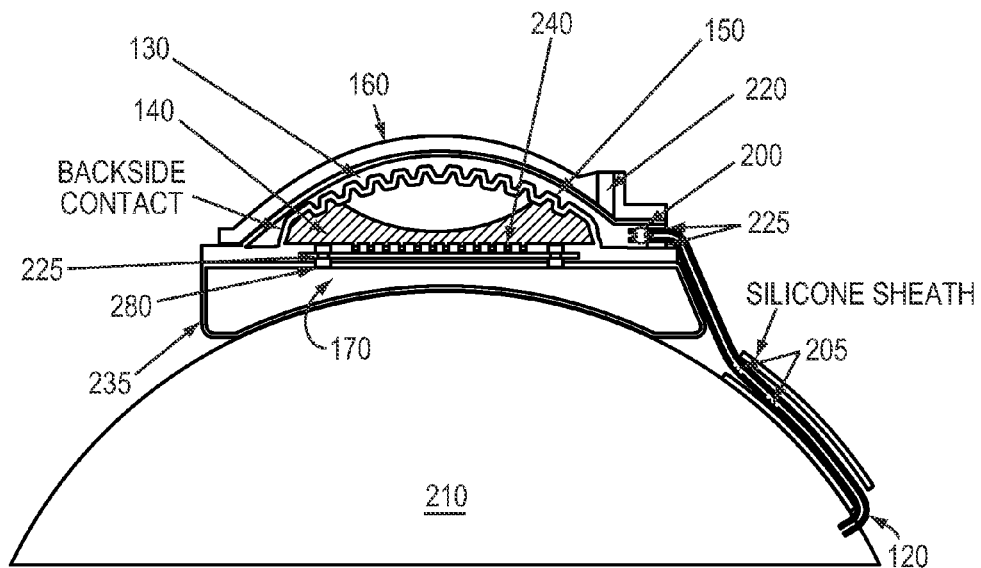
FIG. 4B shows a schematic sectional view of another drug-delivery pump implanted in a patient's eye, in accordance with one embodiment of the invention.

With reference now to FIGS. 4A and 4B, in one embodiment, one or more refill ports 220 are placed in fluid communication with the drug reservoir 130. As illustrated in FIG. 4A, the refill port 220 may be assembled with the drug reservoir 130 and sealed by a sealant (e.g., a biocompatible epoxy) 225 both to the wall 110 defining the drug reservoir 130 and to the protective shell 160. Alternatively, as illustrated in FIG. 4B, a hole may be formed through the protective shell 160 and the refill port 220 featured therein. In still another embodiment, the refill port 220 may be formed elsewhere on the pump 100 and be connected to the drug reservoir 130 through tubing. For example, the refill port 220 may be molded from biocompatible materials, coupled to a matching notch on a hermetic case 235 shown in FIG. 4B and connected to the drug reservoir 130 through the tubing. In one embodiment, the tubing is inserted through a fluid connection port formed in the wall 110 surrounding the drug reservoir 130 and bonded thereto by way of a biocompatible epoxy glue. In either case, the refill port 220 is in fluid communication with the drug reservoir 130 and permits an operator of the pump 100 (e.g., a physician) to refill the drug reservoir 130 in situ (e.g., while the pump 100 is implanted within the patient's eye 210). In general, the drug reservoir 130 can be refilled by inserting a refill needle into and through the refill port 220. An additional drug refill port may, in certain exemplary embodiments, be placed in fluid communication with the bottom chamber 140.

Referring still to FIGS. 4A and 4B, pumping action, including the closed-loop control process, may be controlled by the control circuitry 170. In one embodiment, an induction coil 260 permits wireless (e.g., radio-frequency (RF)) communication with an external controller (e.g., a portable control handset), which may also be used, for example, to charge the battery of the control circuitry 170. The external controller may be used to send wireless signals to the control circuitry 170 in order to program, reprogram, operate, calibrate, or otherwise configure the operation of the pump 100. The control circuitry 170 may, for example, communicate electrically with the electrolysis electrodes 240 in the bottom electrolysis chamber 140 by means of metal interconnects 280 spanning the bottom wall of the electrolysis chamber 140. In one embodiment, the electrolysis electrodes 240 are platinum. Alternatively, any other appropriate conductive material (e.g., copper, gold, or silver on parylene, ceramic, or a biocompatible insulator) may be used. Additional catalyst elements 290 (e.g., constructed from platinum) may be located within the bottom electrolysis chamber 140 to act as a recombination catalyst to encourage the phase change of the electrolyte from its gaseous state to its liquid state when the electrolysis electrodes 240 are turned off. The electrolyte fluid contained within the bottom electrolysis chamber 140 may be a saline (i.e., NaCl and $H_2O$) solution, a solution that contains either magnesium sulfate or sodium sulfate, or may be pure water or any non-toxic solution. During recombination, some gases may diffuse out of the first chamber.

In one embodiment, a plurality of suture holes 295 are incorporated into the outer shell 160 of the pump 100 to provide a means of quickly and stably attaching the pump 100 to a body portion at a treatment site. The suture holes 295 may include loops of material, such as, but not limited to, parylene, that extend from one or more portions of the shell 160 and provide anchoring locations at which a surgeon can suture the pump 100 at a treatment site to stably secure the pump 100 in place. In one embodiment, a glue and/or other affixation method may be used in addition to, or instead of, a suture/suture hole 295 affixation arrangement to hold the pump 100 in place at the treatment site.

Figure 5:
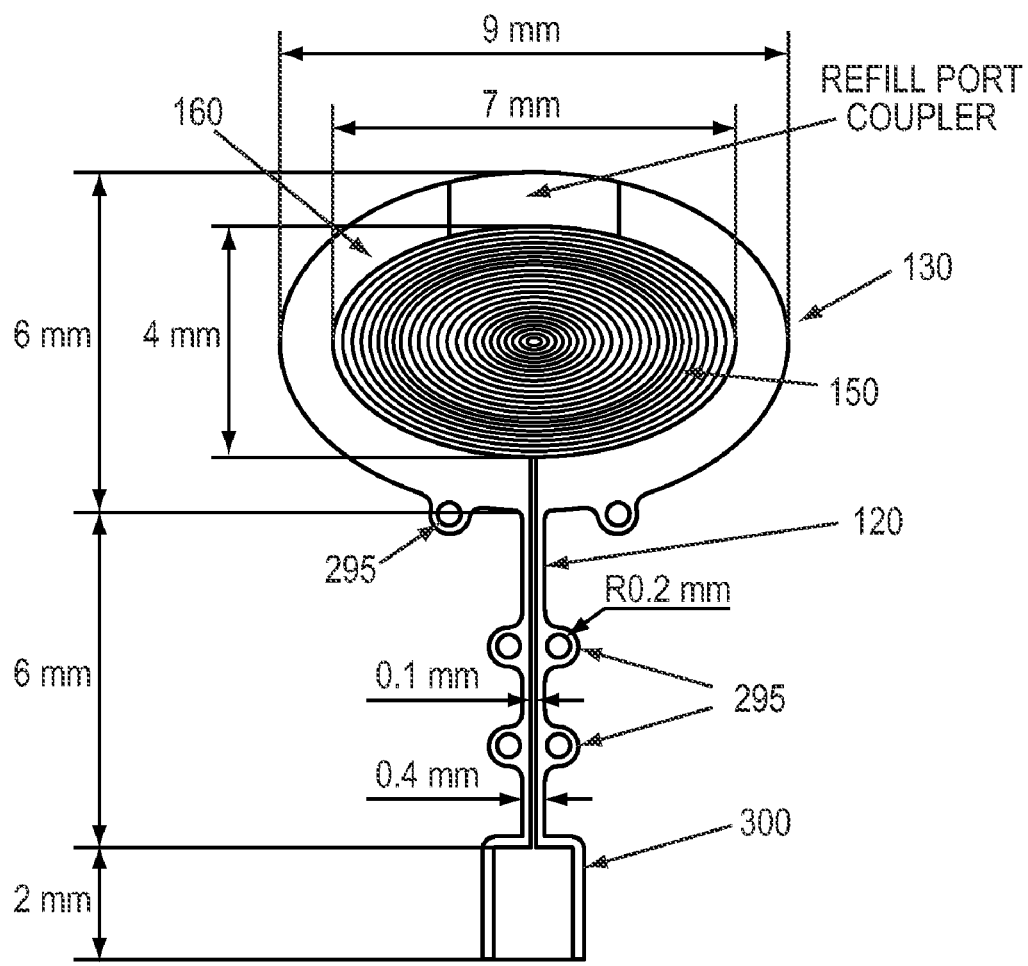
FIG. 5 shows a schematic plan view of another implantable drug-delivery pump, in accordance with one embodiment of the invention.

A plan view of an exemplary pump 100 having a cannula 120, suture holes 295, and a check-valve coupler 300 for affixing a check-valve, is shown in FIG. 5. The coupler 300 facilitates affixation of the cannula 120 to a separate check-valve assembly by mechanical and/or adhesive means. The illustrated pump 100 includes six suture holes 295 positioned at an outer edge of the shell 160 and along the length of the cannula 120 to facilitate affixation of the pump 100 at a treatment site. The suture holes 295 may have an inner diameter, for example, of 400 μm and an outer diameter of 800 μm, although larger or smaller suture holes may be used. Additionally, a greater or lesser number of suture holes 295 may be used, and the suture holes 295 may be located at any appropriate location on the shell 160 and/or cannula 120 of the pump 100.

In an exemplary embodiment, the parylene layers used to form the diaphragm 150 and/or other pump layers have a 20 μm thickness. As illustrated in FIG. 5, the outer dimensions of the drug chamber 130 may form a substantially elliptical shape having dimensions of 9 mm×6 mm, while the outer dimensions of the corrugated diaphragm 150 may form an elliptical shape having dimensions of 7 mm×6 mm. The delivery cannula 120 may be 6 mm long and 400 μm wide, with an inner channel dimension of 20 μm×100 μm. In alternative embodiments, larger or smaller pumps and/or components thereof may be used, and the pump 100 may have any appropriate geometrical shape including, but not limited to, an ellipse, a circle, a square, or a rectangle.

Figure 6:
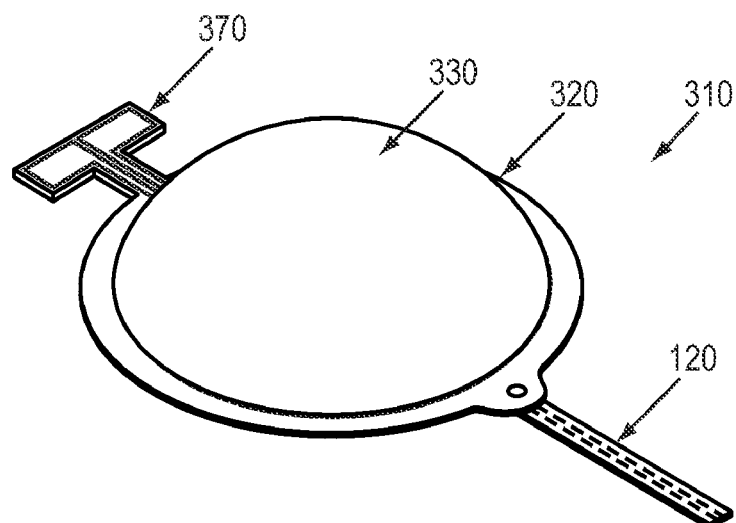
FIG. 6 shows a schematic perspective view of another implantable drug-delivery pump, in accordance with one embodiment of the invention.
Figure 7:
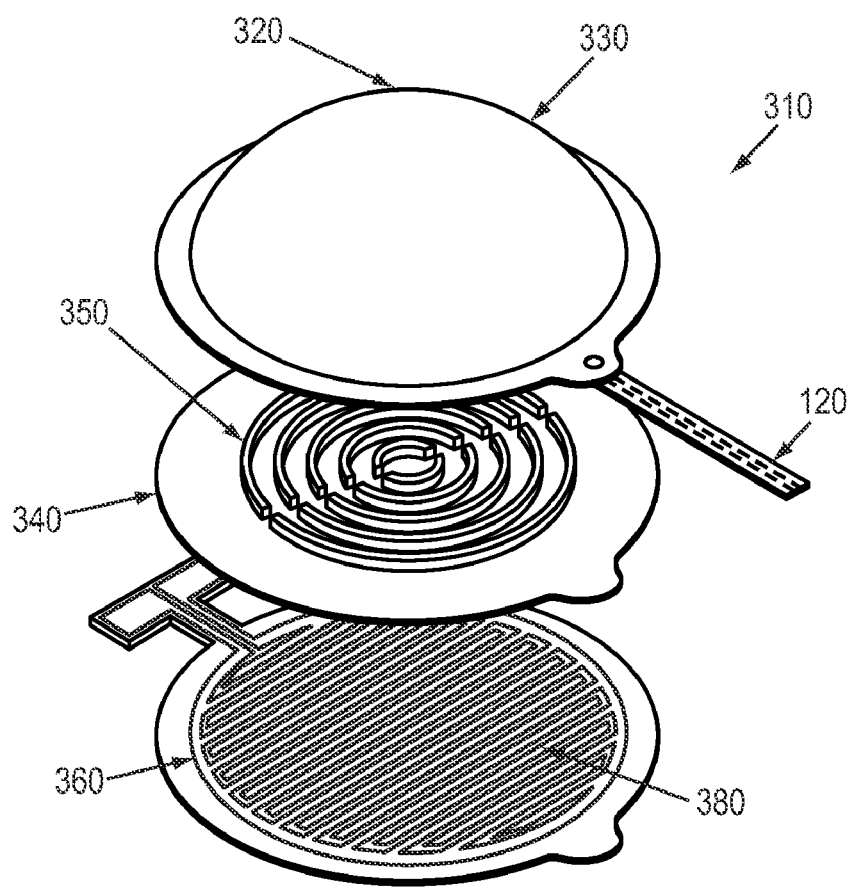
FIG. 7 shows an exploded schematic perspective view of the pump of FIG. 6.

A perspective view of an exemplary implantable pump 310 is shown in FIG. 6, while an exploded perspective view of the pump 310 is shown in FIG. 7. In this embodiment, the pump 310 includes a top layer 320 including a domed portion 330 with a cannula 120 attached thereto. A middle deflection layer 340 forms the diaphragm 150 dividing the drug chamber from the electrolysis chamber. As discussed above, this diaphragm 150 may include corrugations 350 to facilitate expansion and contraction of the diaphragm 150 in response to electrolysis of gas from the electrolytic fluid in the electrolysis chamber. In an alternative embodiment, the diaphragm 150 may have a bellows type structure in addition to, or in place of, the corrugations 350. The layers forming the pump 310 may include, or consist essentially of, parylene.

The pump 310 further includes a bottom layer 360 with electrolysis electrodes 380 coupled thereto or embedded therein. The electrolysis electrodes 380 are coupled to integrated control circuitry 370 for providing power to the electrolysis electrodes 380, and thereby controlling the pumping of fluid from the drug chamber. The circuitry 370 may be located in the same plane as the electrolysis electrodes 380 or may be positioned below the electrolysis electrodes 380. The three Parylene layers 320, 340, and 360 may be bonded together using thermal bonding, or through other appropriate bonding techniques including, but not limited to, chemical bonding, epoxy bonding, and/or pressure bonding. A drug chamber is formed between the top layer 320 and the middle deflection layer 340, while the electrolysis chamber is formed between the middle deflection layer 340 and the bottom layer 360.

One or more openings (not shown) may be left for filling electrolyte and drug separately into the electrolysis chamber and the drug chamber. The opening may then bonded and the chambers sealed, e.g., by thermal bonding. Alternatively, as described above, one or more refill ports that utilize a one-way valve can be incorporated to allow for filling/refilling, flushing, etc. of the drug and/or electrolysis chambers.

A pump 100, 310 may, if desired, include multiple cannulas 120 arranged to extend from one or more locations on the pump 100, 310 toward multiple treatment sites surrounding the pump 100, 310. In one embodiment, each cannula has a separate check valve 220, pressure sensor, chemical sensor, and/or flow sensor 205 associated therewith. In an alternative embodiment, a check valve 200 may be used to control the flow through multiple cannulas 120, and/or a single pressure sensor and/or flow sensor 205 may monitor conditions within multiple cannulas 120. For example, the cannulas 120 may surround the dorsal nerve root of a recently fused spine, with the pump 100, 310 impelling steroids for an extended period (e.g., six months) after surgery to reduce inflammation, improve healing time, and lower pain (and possibly the need for another surgery). Furthermore, the device can be superficially placed just below the fat pad, allowing a minimally invasive procedure to be performed to explant the device with limited risk and cost to the patient (compared to the cost/risk of removing a larger drug-delivery device or long catheter). In an alternative embodiment, no cannula is required, with the drug being pumped through one or more holes/perforations in one or more walls of the drug chamber 130 directly into the surrounding body.

One embodiment of the invention includes a pump 100 including multiple drug chambers 130 each of which can be associated with separate electrolysis chambers 140 or be driven be a single electrolysis chamber 140. Separate cannulas 120 and/or refill ports 220 may be associated with each of the plurality of drug chambers 130. One embodiment of the invention may include a plurality of electrolysis chambers 140, with separate electrolysis electrodes 240 associated therewith. Refill ports 220 may be placed in fluid communication with one or more of the chambers 130, 140.

In one embodiment, the diaphragm 150 is controllably expanded toward a drug chamber 130 using other methods in addition to, or in place of, inducing gas electrolysis from a fluid held within an electrolysis chamber. Such methods may include, but are not limited to, mechanically driven means (e.g., threaded motors), electro-magnetically driven means, pneumatic means, or combinations thereof.

Figure 8:
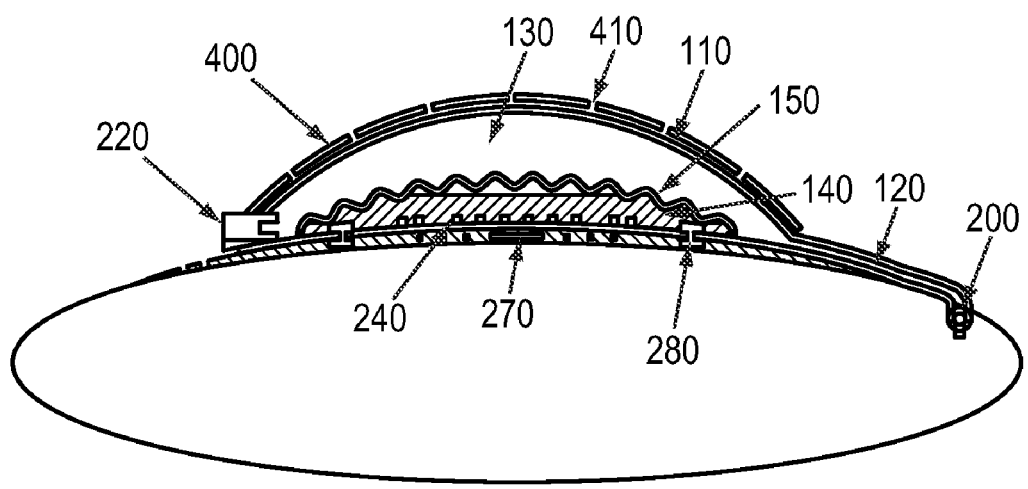
FIG. 8 shows a schematic sectional view of an implantable drug-delivery pump having a perforated shell, in accordance with one embodiment of the invention.

With reference now to FIG. 8, one embodiment of the invention includes an implantable drug-delivery pump 100 having a drug chamber 130 and an electrolysis chamber 140 with a perforated shell 400 positioned above the drug chamber 130. The perforated shell 400 provides protection for the pump components while allowing a body fluid to flow through the perforated shell 400 to offset any vacuum pressure generated on the surface of the drug chamber 130 as the volume of drug within the drug chamber 130 is reduced through the pumping of the drug through the cannula 120 and into a treatment site.

More specifically, as drug is pumped from the drug reservoir 130 and less fluid is left therein, vacuum pressure is generally generated on the outer wall 110 of the drug chamber 130. This pressure resists fluid outflow from the drug chamber 130, thereby increasing the force that must be exerted by the expanding membrane 150 to expel fluid from the drug chamber 130. In addition, because of the reduced drug volume held within the drug chamber 130 after dosing, and the closed check valve 200 in the cannula 120 preventing fluid from returning up the cannula 120 towards the drug chamber 130, vacuum pressure may also be generated against the drug chamber 130 as the diaphragm 150 of the electrolysis chamber 140 returns to its original position. By providing the protective shell 400 having one or more perforations 410 to permit ingress of surrounding body fluid into the space between the shell 400 and the outer wall 110 of the drug chamber 130, the vacuum pressure exerted on the drug chamber 130 is automatically balanced by the inflowing bodily fluid, thereby maintaining a consistent actuation time and conserving battery power.

The protective shell 400 may be a substantially solid shell, while the perforations 410 may be of any size, shape, and/or number necessary to provide a sufficient flow rate from the surrounding bodily fluid into the cavity between the shell 400 and the drug chamber 130. The perforations 410 may cover the entire portion of the shell 400 covering the drug chamber 130, or only a portion thereof.

The shell 400 may include, or consist essentially of, polypropylene. Alternatively, the shell 400 may include, or consist essentially of, any other appropriate material such as, but not limited to, a biocompatible plastic material, a metal (e.g., titanium, niobium, tantalum), or other material providing sufficient rigidity and mechanical strength to protect the pump 100 while exhibiting sufficient biocompatibility to be placed within a patient for an extended period. In one embodiment, the shell 400, or a portion thereof, has a thickness greater than 0.1 mm. The perforated shell 400 may be at least partially coated by a coating such as, but not limited to, a biocompatible material (e.g. parylene).

The perforated shell 400 has three main functions: mechanical protection, balancing vacuum pressure in the drug chamber 130, and integration of the refill port 220. In particular, the hard shell 400 provides protection against mechanical damage during implantation, refilling, or at any time that the pump 100 is exposed to large pressures (which, if transmitted to the drug chamber 130, may cause unwanted delivery of the drug). The mechanical strength of the shell 400 can be designed and optimized by selecting different materials, shell thicknesses, 3-D profile, and geometry (e.g., shape, size, etc.) and distribution of the perforations 410.

The perforations 410 may be large enough to create minimal resistance to fluid inflow and outflow, but small enough to provide adequate protection against mechanical damage. For example, in some embodiments, the perforations 410 have diameters smaller than the diameter of a refill needle, thereby preventing its entry. In other embodiments, the perforations 410 are larger but covered, so that a uniformly solid exterior is presented to external objects that approach the pump 100. For example, each perforation 410 may have an overlying cover, which is larger in diameter than the perforation 410 and supported thereover by pillars or other appropriate structures. Alternatively, the cover may be supported over a perforation 410 by a mesh or screen. In one embodiment, the shell 400 comprises a meshed and/or woven structure.

Figure 9:
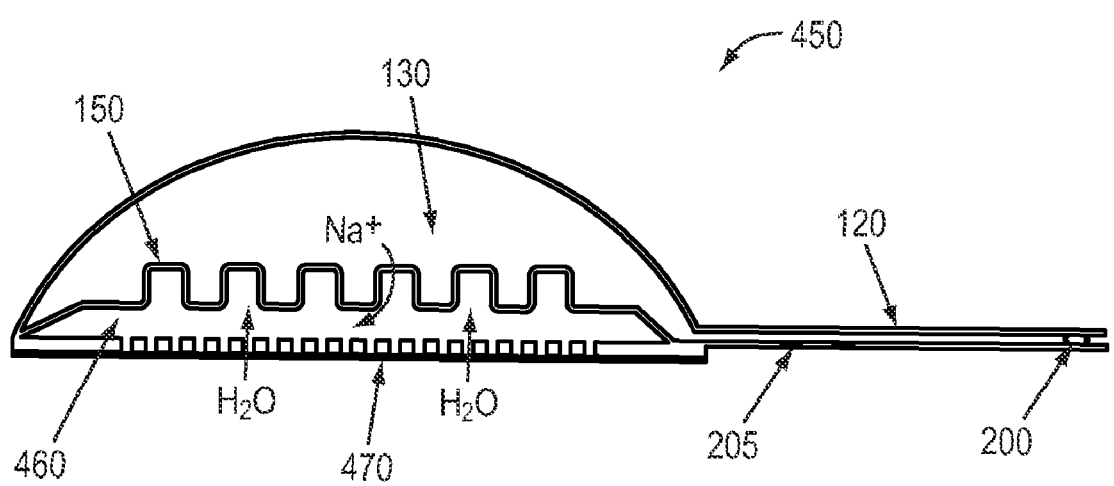
FIG. 9 shows a schematic sectional view of an osmosis-driven implantable drug-delivery pump, in accordance with one embodiment of the invention.

With reference now to FIG. 9, one embodiment of the invention includes an implantable drug-delivery system including a pump 450 driven by a passive osmosis-based mechanism. Implantable drug-delivery systems that utilize a passive mechanism for drug delivery can eliminate or limit the need for control electronics and power sources, thereby potentially reducing size, cost, complexity, safety, biocompatibility concerns, etc. Such pump-delivery systems can be placed in proximity to the surgical site after a surgical procedure, enabling targeted dispensing of a drug through one or more cannulas 120 in a localized region. In particular, active or passive osmotic pumps can be beneficial to ocular applications by lowering the size, cost, and power requirements over existing pumps, while still delivering active medication directly to the anterior or posterior chamber or subretinal area.

In addition, some traditional drug-pump cannulas may be subject to biofouling, or the clogging of tissue and cells in the cannula, which prevents the outflow of drug- particularly in devices where considerable time elapses between bolus injections. For example, if a drug pump only impels drug every 24 hours, it is almost always dormant, and therefore debris and cells can clog the system, making it less efficient or plugging the outflow. By providing an osmotic pump with continuous outflow of drug, biological debris can be prevented from collecting due to the continuous operation of the device.

In one embodiment, the osmosis-driven pump 450 includes active electronics, powered by a battery or inductive telemetry, to control the opening and closing of an active check valve 200, thereby achieving active control of the pulsatile delivery of the osmotic device, while still keeping overall system power requirements below those of, for example, electrolysis-based pumps.

In the exemplary embodiment shown in FIG. 9, the osmotic drug-delivery pump 450 includes a drug chamber/reservoir 130 containing one or more drugs or other therapeutic delivery agents. A cannula 120, or other tube or orifice, is in fluid communication with the drug chamber 130 to facilitate accurate delivery of a drug held within the drug chamber 130 to a targeted treatment site within a patient. The pump 450 further includes an osmosis chamber 460 containing a solvent (e.g., water) and solute (e.g., NaCl). A membrane 150 (e.g., a corrugated, elastic, and/or bellows membrane) separates the osmosis chamber 460 from the drug chamber 130.

At least a portion of an outer wall of the osmosis chamber 460 includes a permeable or semi-permeable membrane 470 that, for example, permits passage of the solvent but is not (or is minimally) permeable to the solute contained in the osmosis chamber 460. In one embodiment, the permeable membrane 470 is manufactured as part of the osmosis chamber 460. In an alternative embodiment, the permeable membrane 470 is manufactured separately and integrated with the chamber 460 in a separate step.

In operation, placing the pump 450 in a solvent (e.g., implanting the pump 450 in the body, the solvent consisting of biological fluids surrounding the pump 450) results in a net flux of the solvent across the permeable or semi-permeable membrane 470. The magnitude of the flux is determined in part by the degree of permeability of the membrane 470 to the solvent. This net flux results in a flow of solvent (e.g. water) into the osmosis chamber 460 from the surrounding body, which in turn increases the pressure in the osmosis chamber 460. The increase in pressure deflects the membrane 150 into the drug chamber 130, thereby decreasing its volume and forcing the drug held within the drug chamber 130 through the cannula 120 and out to the targeted treatment site.

In one embodiment, the pump 450 includes other (e.g., biocompatible) components, such as a protective shell, housing, enclosure, or covering, that provide protection to, and/or help maintain the structural integrity of, the pump 450. Other components that may be incorporated into the pump 450 include refill ports for one or both of the chambers 130, 460, one or more flow and/or pressure sensors 205, and/or one or more check-valves 200 to prevent back-flow. The pump 450 may also incorporate active electronics, e.g., to monitor flow rate of the drug, record dosing schedules, and/or ensure proper function.

As described further below, the osmotic drug-delivery pump 450 may be monolithically microfabricated utilizing multiple polymer layers that are later bonded together using any of a number of common packaging techniques (e.g., thermal bonding of the layers). In one embodiment, the pump 450 utilizes parylene or other biocompatible material to achieve an active device with full biocompatibility. For example, the drug chamber 130, cannula 120, and check valve 200 may all be formed from one or more parylene sheets. In one embodiment, the pump 450 is flexible and easy to fit into a protective shell with optimized implantation 3D geometry.

Figure 10:
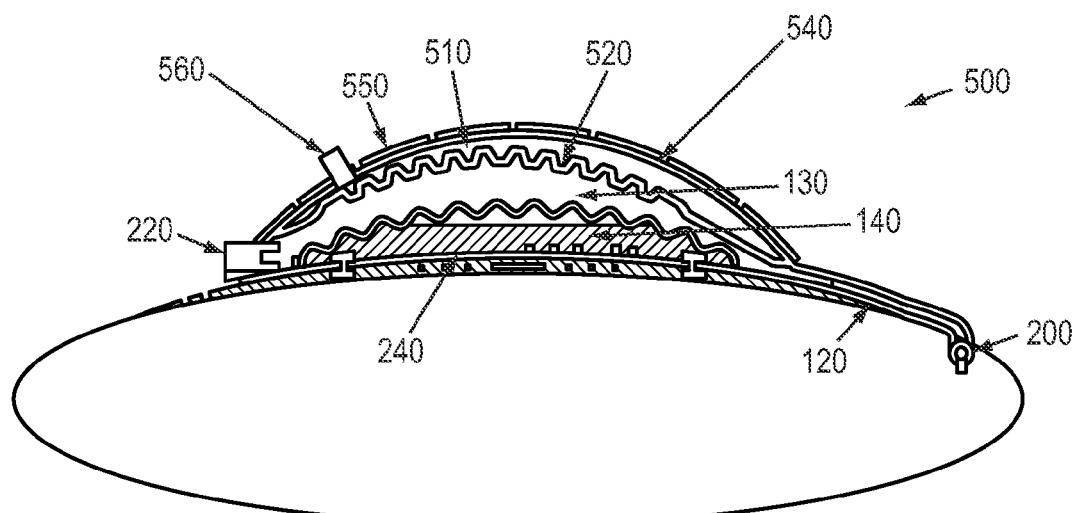
FIG. 10 shows a schematic sectional view of an implantable drug-delivery pump having an osmosis chamber, in accordance with one embodiment of the invention.
Figure 11:
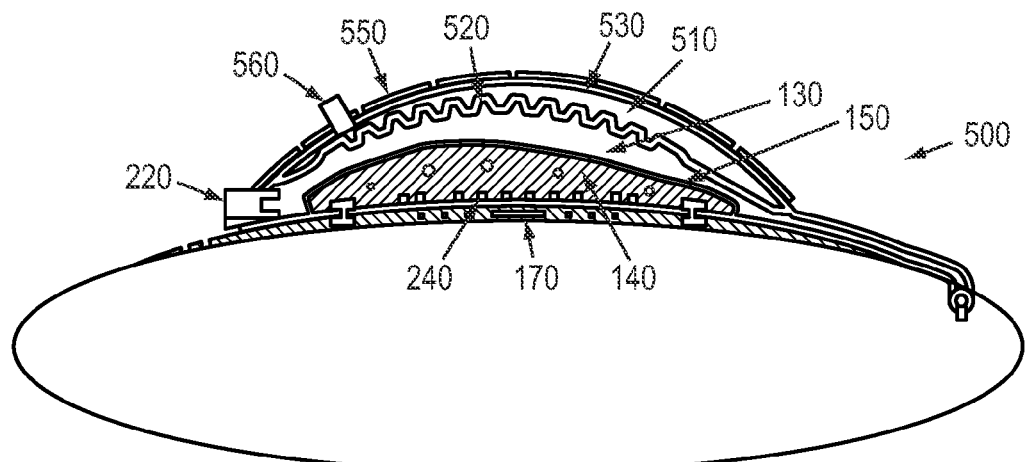
FIG. 11 shows a schematic sectional view of the pump of FIG. 10 during activation of electrolysis electrodes.
Figure 12:
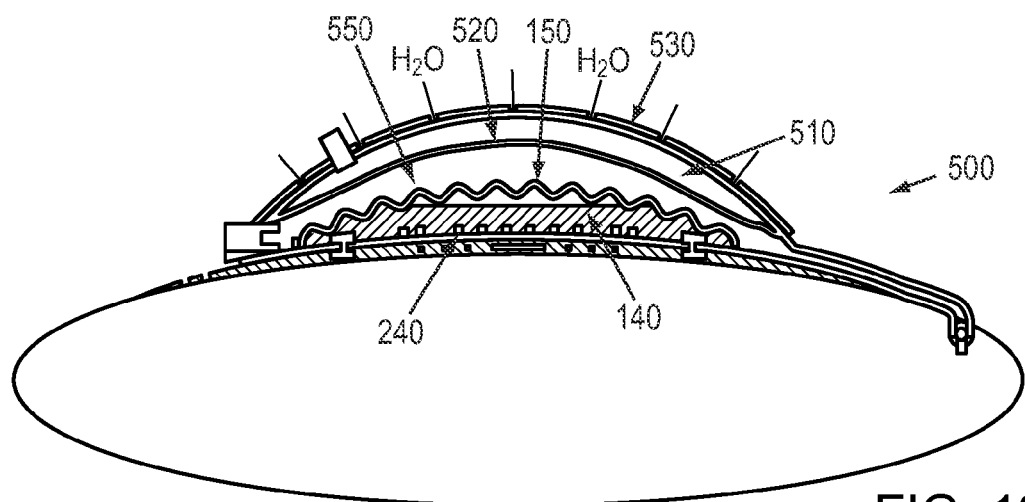
FIG. 12 shows a schematic sectional view of the pump of FIG. 10 after de-activation of the electrolysis electrodes.

With reference now to FIGS. 10-12, another embodiment of the invention includes an implantable drug-delivery system including a pump 500 having an osmosis chamber 510 to prevent, as earlier described, the accumulation of vacuum pressure on the drug chamber 130. This osmosis chamber 510 may be utilized to automatically balance a vacuum pressure on the drug chamber 130 after each electrolysis dosing, thereby maintaining a consistent actuation time and conserving battery power. As also illustrated in FIGS. 10-12, the pump 500 includes an electrolysis chamber 140 and electrolysis electrodes 240, as described hereinabove.

The osmosis chamber 510 overlies the drug chamber 130 and these two chambers are separated by a fluid barrier such as, but not limited to, a corrugated diaphragm 520. The top layer 530 of the osmosis chamber 510 may include a thin-film, semi-permeable osmotic membrane 540 that may, in one embodiment, be integrated with (e.g., uniformly attached to) a perforated protective hard shell 550. The perforations expose the osmotic membrane 540 to surrounding fluid. In an alternative embodiment, no permeable hard shell 550 is required, with the semi-permeable osmotic membrane 540 itself being structured with sufficient strength and rigidity to provide a protective covering for the pump 500. In one embodiment, one or more of the chambers 130, 140, 510 include a refill port in fluid communication therewith. For example, a refill port 560 may be coupled to the osmosis chamber 510, and may, for example, be mounted through the hard shell 550. The osmosis chamber 510 may be filed with a fluid such as, but not limited to, a solute and solvent (e.g., NaCl in water). Fluids that may be used in the osmosis chamber 510 also include a saline solution, a solution including magnesium sulfate, a solution including sodium sulfate, pure water, or any non-toxic solution.

Again, in operation, when current is supplied to the electrolysis electrodes 240, the electrolyte generates electrolysis gas, expanding the diaphragm 150, and forcing liquid out of the drug chamber 130 through the cannula 120. When the current to the electrolysis electrodes 240 is stopped, and the gas dissipates back into its liquid state within the electrolysis chamber 140, the corrugated diaphragm 150 above the electrolysis chamber 140 recovers its space-efficient corrugations. Because of the reduced drug volume after dosing and the closed check valve 200 in the cannula 120, vacuum pressure is generated against the drug chamber 130 as the diaphragm 150 above the electrolysis chamber 140 returns to its original position.

To counteract this vacuum pressure, fluid (e.g., water) from surrounding bodily fluids flow through the permeable membrane 540 and into the osmosis chamber 510. More specifically, the osmosis chamber 510 may initially be charged with a liquid that is hypertonic relative to the external bodily fluid. As a result, water tends to flow through the osmotic membrane 540 and into the osmotic chamber 510. The incoming water equalizes the pressure on both sides of the upper drug chamber membrane 520, with the equalized pressure in the drug chamber 130 helping to reduce the deflection of the diaphragm 150 necessary to generate a check valve cracking pressure, therefore saving pump operation power.

In one embodiment, when the pump 100 is in rest status, osmotic pressure will reach balance with the drug chamber 130 pressure, which is lower than a check valve cracking pressure, until the next dosing which creates lower pressure in the drug chamber 130, after which a new balance status will be reached. The concentration of the osmosis chamber is selected such that the balance pressure after the final dosage won't exceed a check valve cracking pressure.

The osmotic pressure driving the flow depends on the solute concentration in the osmotic chamber 510 (relative to the surrounding fluid) and the degree of permeability of the membrane 540. In one embodiment, the solute concentration in the osmotic chamber 510 is low enough to keep the osmotic pressure well below the cracking pressure of the cannula check valve 200 (so that fluid is never improperly expelled from the drug chamber 130).

As water fills the osmosis chamber 540, in effect replacing the volume of drug pumped out of the drug chamber 130 after each dosage, the concentration of osmotic solute decreases. Accordingly, while the initial solute concentration cannot be so high as to cause fluid to be driven out of the drug chamber 130, it should be sufficiently high that, despite its gradual dilution, it remains adequate to draw liquid through the osmotic membrane 540 until the supply of drug has been fully dispensed. At that point, the drug chamber 130 may be refilled through the refill port 220, and the osmosis chamber 510 is purged and refilled with the hypertonic liquid through the osmosis chamber refill port 560. In one embodiment, filling the drug chamber 130 with the osmosis-chamber refill port 560 open may accomplish the necessary purging of the osmosis chamber 510.

In another embodiment, the invention includes an outer package to provide a protective enclosure for at least a portion of the pump. Exemplary packages 600 are shown in FIGS. 13 through 19. The package 600 may be manufactured, at least in part, from materials such as, but not limited to, a metal (e.g. titanium, tantalum, or niobium), an alloy (e.g. nitinol (TiNi)) polypropylene, polyimide, polyetheretherketone (PEEK), glass, ceramic, and/or epoxy. Depending on the material used and the shape desired, the shell may be fabricated using techniques such as, but not limited to, computer numerical control (CNC) milling, stamping, extrusion, and/or injection molding. The package 600 may be at least partially coated by a coating such as, but not limited to, a biocompatible material (e.g. parylene).

Figure 13:
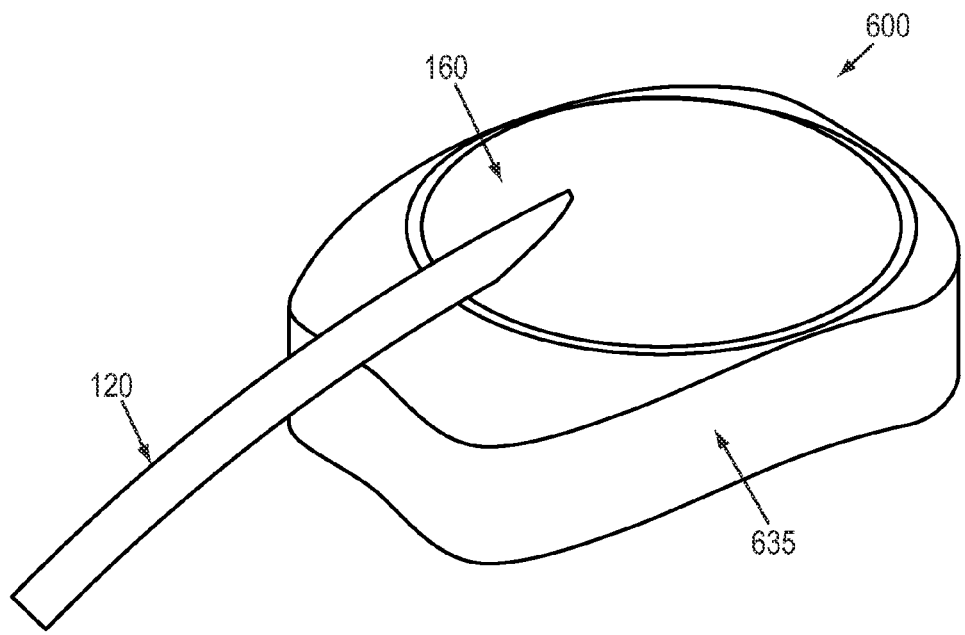
FIG. 13 shows a schematic perspective view of a shell for a pump, in accordance with one embodiment of the invention.
Figure 14:
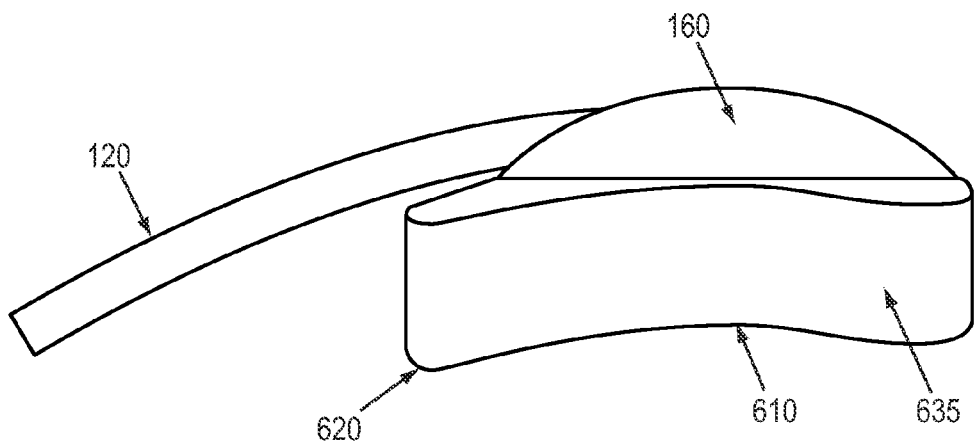
FIG. 14 shows an elevational view of the pump of FIG. 13.
Figure 15:
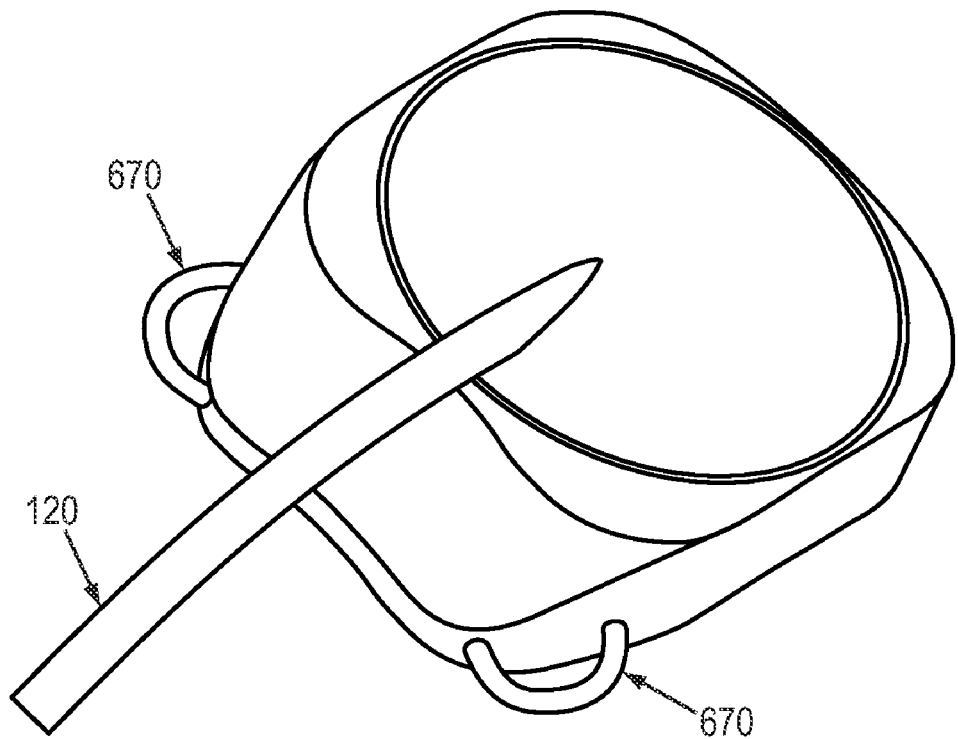
FIG. 15 shows a perspective view of a shell for a pump with suture eyelets, in accordance with one embodiment of the invention.
Figure 16:
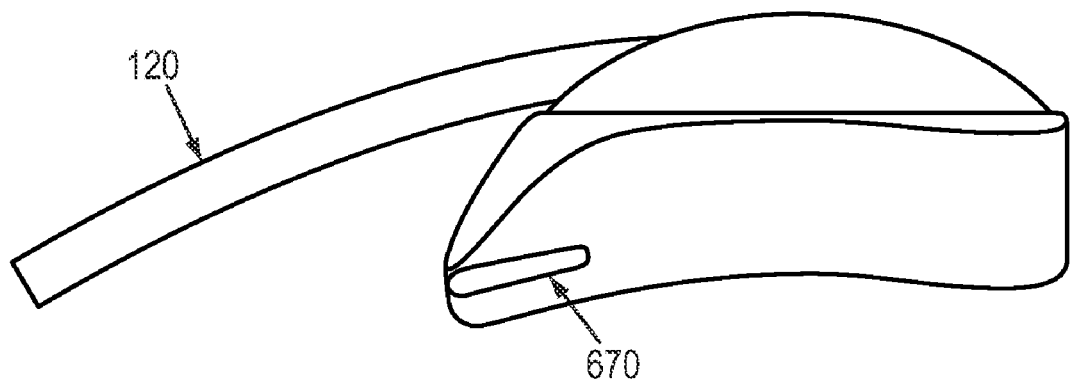
FIG. 16 shows a schematic side view of the pump of FIG. 15.
Figure 17:
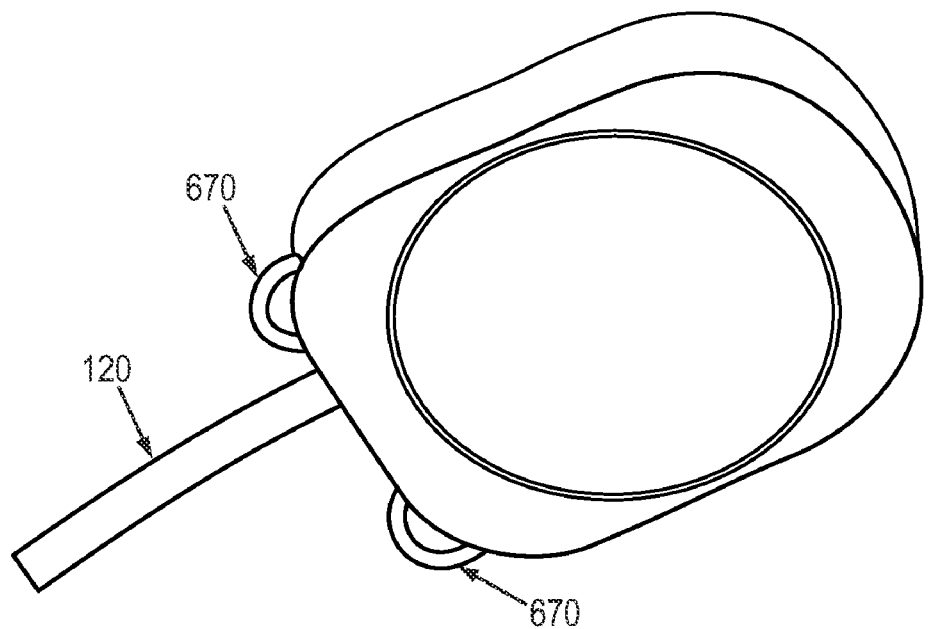
FIG. 17 shows another schematic perspective view of the pump of FIG. 15.

A first exemplary package 600 for an implantable drug-delivery pump is shown in FIGS. 13 and 14. In this embodiment, the package 600 includes a hermetic enclosure 635 and a dome-shaped protective shell 160 that has a recessed shape (including a concave lower portion 610) that may be obtained through, for example, hydraulic stamping or CNC-machining. The dimensions and height of the device depend on the function, location, size of electronics and power source, etc., and can be tailored to a specific application and/or patient. In one embodiment, the package 600 is designed for intra-ocular deployment and has dimensions of approximately 14 mm (L)×10 mm (W)×4 mm (H). In alternative embodiments, smaller, larger, or differently proportioned shells may be utilized. The hermetic enclosure 635 may provide a housing containing elements including, but not limited to, the control electronics, a power source, and/or a communication means, as described herein. Elements such as the electronics and power source may be disposed within the hermetic enclosure 635 in a stacked configuration to provide a smaller footprint, or side-by-side to provide a shallower form factor.

In one embodiment, the hermetic enclosure 635 includes an endplate 620 enclosing the recessed area, which can be attached thereto in a manner suited to the material, e.g., welding or bonding, to provide a hermetic seal. The hermetic enclosure 635 (or another surface of the enclosure) may include feed-through elements to allow electrical connections to span the internal electronics and external elements accessible outside the hermetically sealed pump. These external elements may include, for example, a coil for a wireless charging/telemetry link, the electrolysis electrodes and sensor connections in the pump, and/or the electrodes in a stimulation device, etc. Removal of the endplate 620 facilitates access to these "external" components. The coil may be molded to the package 600. Alternatively, the hermetic enclosure 635 may be fabricated from injection-molded plastic or potted epoxy, such that all of the electronics and power source are hermetically encased within the hermetic enclosure 635 as it is manufactured so that no separate endplate is necessary. For example, in one embodiment the hermetic enclosure 635 includes an upper an lower surface that are hermetically sealed together after placing the circuitry 170 and/or other components therein.

One or more cannulas 120 may extend through the shell and be in fluid communication with one or more drug chambers housed within the package 600. The cannula(s) 120 may be of any appropriate length, diameter, and curvature as required to deliver drug to a particular treatment site. In one embodiment, a silicone or similar tube is added around the cannula 120 (and may be backfilled with a silicone-type adhesive) for added strength/durability and/or to create rounded edges to minimize irritation to surrounding tissue and at the incision/point of entry (e.g., into the vitreous cavity).

The shape and size of the package 600 are dictated by its function and can be designed to suit any particular geometry. For example, in one embodiment, the package 600 houses an intra-ocular drug pump and is shaped to match the curvature of an eyeball upon which it is to be surgically mounted. This may be achieved by milling, injection molding (in the case of polymers such as polypropylene), or by doming the structure, e.g., with a hydraulic press and tooling (in the case of a metal such as titanium). The endplate 620 can be shaped to match the curvature of the package 600 so that the interior volume of the package 600 remains constant. In another embodiment, the thickness and/or width of the package 600 are tapered, providing a teardrop shape. The profile and edges of the package 600 may be rounded to minimize the risk of damage to tissue structures in direct contact therewith, as well as to maximize comfort for the patient and ease implantation for the surgeon. For example, the rounded corners and edges (alone or in conjunction with the teardrop shape previously mentioned) on an intraocular drug pump can ease surgical implantation when inserted into an incision in the conjunctiva or sclera of the eye, or the parenchyma of the brain, and also reduce irritation or inflammation at the site of implantation.

In one embodiment, the device is a small drug pump with a protective shell 160 that covers a drug reservoir and an electrolysis chamber. The shell 160 may be made from a durable material such as, but not limited to, titanium, nitinol, tantalum, niobium, polypropylene, polyimide, glass, ceramic, PEEK, and/or epoxy, as described above, and may be added to protect components of the pump, such as, but not limited to one or more drug chambers. The shell 160 may have perforations or holes to permit the influx of a fluid for pressure equalization of the drug chamber of the pump.

A shell 160 (with a drug chamber 130 and electrolysis chamber 140 enclosed thereunder) may be coupled to, and sit atop, the hermetic enclosure 635, enclosing the electronics and battery. The drug chamber 130, electrolysis chamber, and/or protective shell 160 may be attached in a manner suitable to the material of the hermetic enclosure 635, such as, but not limited to, adhesive means. In an alternative embodiment, the shell 160, and pump elements (e.g. drug chamber 130 and electrolysis chamber), may be located adjacent to the hermetic enclosure 635 as opposed to atop the hermetic enclosure 635, thereby reducing the overall height. An example package 600 having a shell 160 (with drug chamber 130 and electrolysis chamber 140 enclosed thereunder) adjacent to the electronics and power source sub-assemblies 660 is shown in FIGS. 20 to 23. Affixation using an adhesive has the advantage, for example, of allowing a two-step sterilization process. For example, it may not be possible to expose the package 600 to gamma radiation (e.g., because it encloses vulnerable electronics or is itself subject to damage), but it can be sterilized with, e.g., ethylene oxide gas. The shell 160 and pump elements, however, may be impervious to ethylene oxide gas but amenable to sterilization with gamma radiation. In such implementations, it is possible to sterilize the shell 160 and pump elements with gamma radiation, attach it to the hermetic enclosure 635 in a sterile environment, and then sterilize the whole package 600 using ethylene oxide.

In one embodiment, the cannula 120 is fed through the shell 160 and the interface between the cannula 120 and the shell 160 sealed with a silicone or other suitable material, e.g., epoxy. This configuration may be beneficial in providing protection to the pump structure without requiring an additional shell above the dome of the pump to add structural support. Similarly, the shell 160 may be encased with the other sub-assemblies in an injection-molded or potted epoxy enclosure. The cannula 120 may be contained within a tubing sleeve made, for example, from silicone or a similar material, to provide additional structural integrity and protection to the cannula 120. This sleeve may be backfilled with a silicone or similar adhesive.

Figure 18:
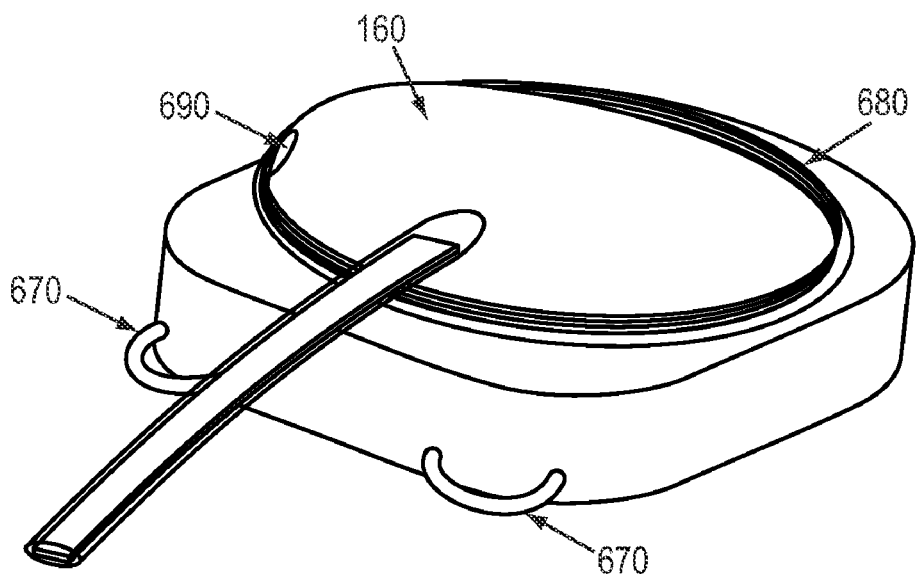
FIG. 18 shows a schematic perspective view of a shell for a pump with suture eyelets and a coil, in accordance with one embodiment of the invention.
Figure 19:
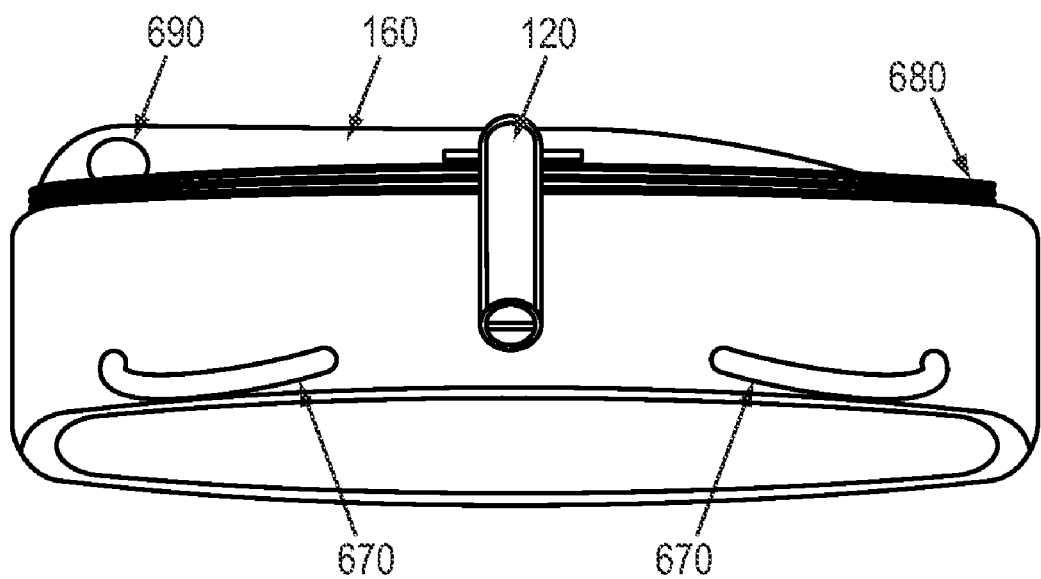
FIG. 19 shows a schematic side view of the pump of FIG. 18.

In the case of a refillable drug pump, in which the drug reservoir is refilled via a needle, the rigid enclosure can also serve as a safety "stop" to prevent the needle from going too far and damaging the device or injuring the patient and/or to assist in guiding the needle into the refill port. As shown in FIGS. 18 and 19, the outer shell may contain a refill port 690 fabricated from silicone or a similar material. The refill port 690 may be located at any appropriate position on the package 600 and provide easy access by a surgeon after implantation, using the rigid shell to prevent over-insertion of the needle or alternately to guide the needle (e.g., a channel in the rigid shell).

As shown in FIGS. 15-19, the shell may include eyelets 670, or other structures extending from the hermetic enclosure 635, for securing the device to a treatment site using sutures. In one embodiment, the eyelets 670 are rounded to prevent irritation or damage to the surrounding tissue, and are located at the top of the device to aid in implanting and securing the device against the eye. This can also be helpful in the brain, spine and knee. In an alternative embodiment, one or more suture eyelets 670 may be positioned at any location around an exterior of a package 600 to allow the device to be secured in place easily by the surgeon. As described above, in one embodiment, the package 600 may include a portion including one or more perforations to enables a fluid flow to pass through the shell to an interior portion thereof to provide pressure equalization, solvent permeation in an osmotic pump, etc.

In one embodiment, as illustrated in FIGS. 18 and 19, the shell is manufactured with one or more coils 680 integrated therein to provide wireless telemetry and/or recharging. This may be achieved, for example, by injection molding of the package 600 with the coil 680 in place.

Figure 24:
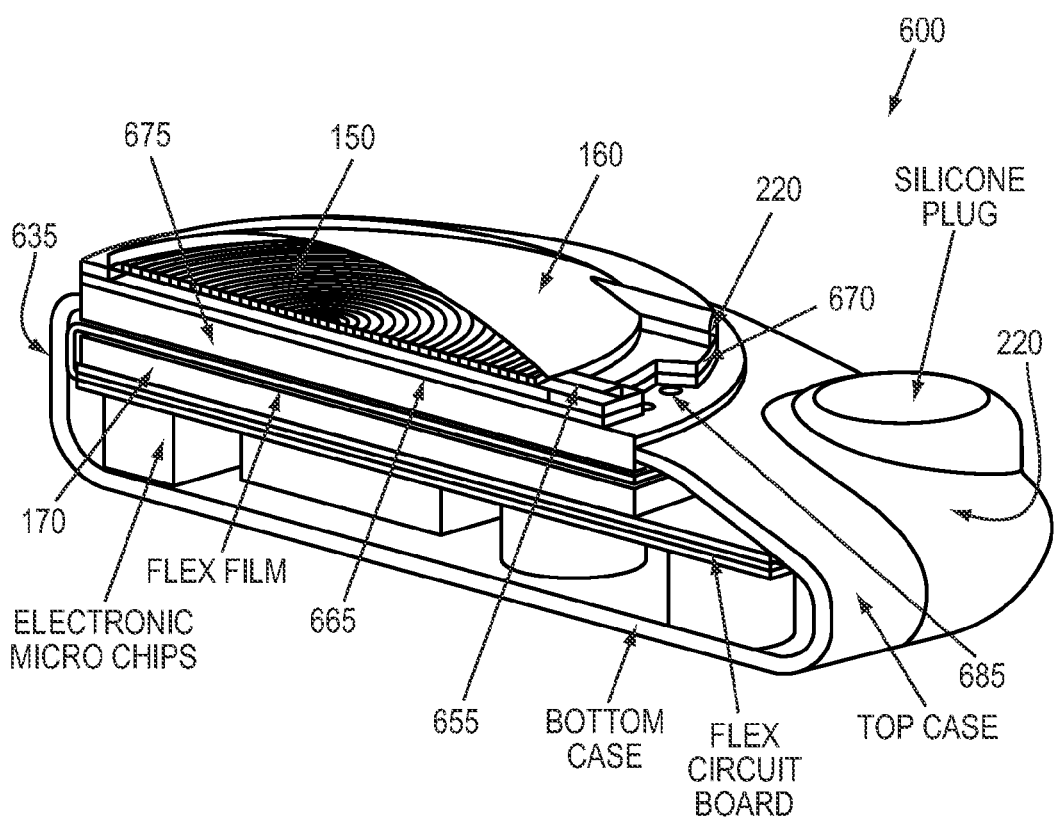
FIG. 24 shows a sectional schematic perspective view of a pump encased within a shell, in accordance with one embodiment of the invention.
Figure 25:
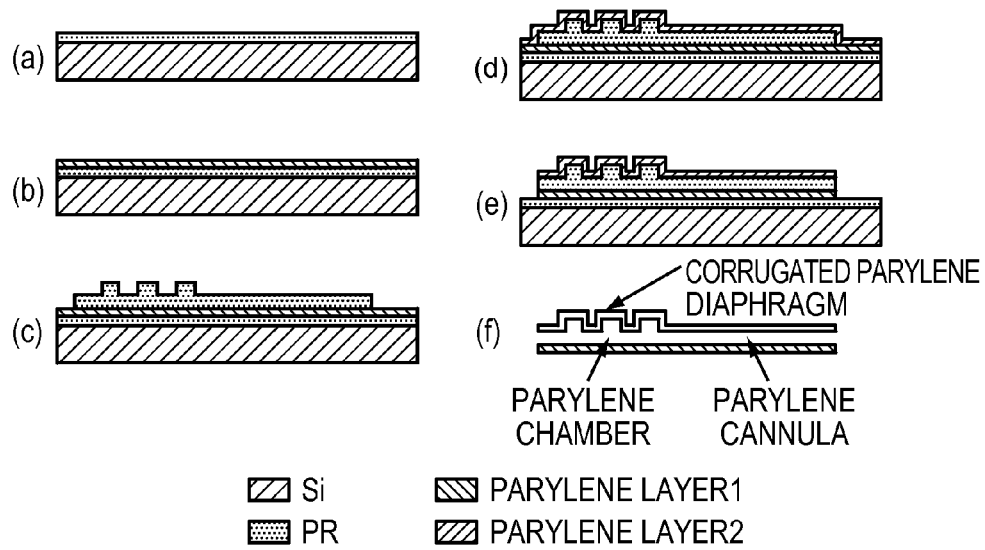
FIG. 25A-25F show steps in the fabrication of a top layer of a drug chamber in accordance with an embodiment of the invention.

FIG. 24 depicts a schematic sectional view of another pump 100 embodiment that has a package 600 including a hermetically enclosure 635 containing the electronics and battery. Here a ceramic header 675 with electrical feedthroughs 685 is brazed to top of the biocompatible metal (e.g. titanium, niobium, tantalum or nitinol) case to form the hermetic enclosure. However, the metal or ceramic alone can form the entire hermetic enclosure 635 with insulated feedthroughs 685 brazed on. The feed-throughs 685 are for the control of the electrolysis electrode, the sensors and/or for the connection to the telemetry coil/antenna (not shown) that is molded on the shell 160. The ceramic electrolysis chip 665 containing the electrolysis electrodes is located on top of the hermetic enclosure 635. A spacer 670 with a set thickness may be placed around and beneath the edge of the diaphragm 150 to create volume. In one embodiment, there is an opening formed in the spacer 670 to create a fill hole for the electrolysis chamber 140 that can be sealed after filling the electrolysis chamber 140 with an electrolyte. A filling tube can be coupled to the fill hole and sealed after filling. The spacer 670 may be formed from a material such as, but not limited to, a metal (e.g. Titanium), ceramic, plastic, and/or other biocompatible material. The top drug reservoir wall 160 may have two fluid ports. One port 655 is to couple with a cannula for drug delivery and the other 220 for connecting with a refill port through a tube (not shown).

A. Electronic Subsystems for Implantable Pumps

Power for the device can be provided by several different technologies including both standard chemical-based batteries and/or capacitors that store a charge in an electric field. It is also possible to provide power via a wireless inductive link instead of on-board power-storage capabilities. (Alternatively, as described below, the inductive link can be used to charge/recharge an on-board battery or capacitor.) The power source may include a coil in an inductive link, which may include a ferrite core.

In some embodiments, the power source is provided by a primary (i.e., non-rechargeable) or secondary (i.e., rechargeable) lithium-based battery (e.g., a lithium-ion, lithium-polymer, or lithium phosphorus oxynitride (LiPON) battery). In one embodiment, the device utilizes a LiPON thin-film solid-state battery, which offers high charge density in extremely thin and small form factors. In addition, the solid-state structure of LiPON is inherently safer than many other lithium and liquid/chemical based batteries that can suffer outgassing, leakage, and even explosion. Providing an extremely thin power source allows, for example, for a flexible design that can fit the curvature of a shell designed for the eye, brain and spine. To increase storage capacity, it is possible to stack several layers of thin-film batteries within a shell.

Due to safety concerns, rechargeable lithium and other batteries, especially those used in implantable medical devices, are typically enclosed in a metal case for protection and biocompatibility. In one embodiment, an a rigid outer enclosure or shell (formed, for example, from a biocompatible material such as, but not limited to, titanium, tantalum, nitinol, or niobium) may encase components of the pump to provide protection for the components. As the protective shell may house both pump components and electronic components such as, but not limited to, the battery, the device electronics and the battery technology may be enclosed in a single, hermetically-sealed shell without the need to provide separate shells for different components. In one embodiment, the battery and electronics power and control a drug pump made from parylene. In a related embodiment, a LiPON battery is deposited on a layer or sheet of parylene that may or may not be integrated with the parylene pump structure.

An energy-storage source suitable for use in connection with a drug pump may include a battery and/or capacitor integrated into the implantable device. In one embodiment, the battery utilizes a LiPON thin film as a lithium electrolyte. LiPON may be advantageous, for example, by providing improved size/geometry, safety, and/or charge capacity than certain other technologies. Using LiPON technology, for example, it is possible to achieve a high charge density in a small form factor, which may be critical for implantable devices. LiPON batteries can also be made extremely thin, allowing for a flexible design that can fit the curvature of an implantable device designed to lie flat against the eye or brain, for example. Because they are inherently thin, several individual cells may be stacked to increase voltage (by connecting the cells in series) or to increase capacity (by connecting them in parallel) while still maintaining a thin profile.

LiPON batteries may be manufactured by depositing thin layers of different materials on a substrate to form the anode, cathode, and electrolyte. After deposition, the layers are typically sealed (e.g., by means of a laminate) in order to prevent chemical reactions caused by interaction with the surrounding air that would significantly shorten the life of the battery. The battery's lifespan can further be extended by installing the battery in a hermetically sealed enclosure containing an inert environment (e.g., argon). In one embodiment of an implantable drug pump, the substrate comprises, or consists essentially of, a polyimide sheet (e.g., KAPTON). The advantage of depositing the battery onto a polyimide sheet is that this substrate can additionally serve as the circuit board for the electronics, providing electrical interconnects between different components that are mounted on the polyimide substrate through standard electronics-manufacturing techniques (solder, conductive epoxy, etc.). Therefore, the battery and electronics are all borne by a single monolithic substrate. For example, the underside of a polyimide sheet can support multiple battery layers while the electronic components and integrated circuits can be mounted on the topside.

In a related example, the battery layers are deposited on a thin sheet of parylene, from which the mechanical pumping mechanism may be formed. This approach also has the benefit of providing a single, integrated structure for the battery and another component of the implant (in this case, the pumping mechanism). In alternative embodiments, the battery layers can be deposited on a sheet of parylene that is not used for any other function. Parylene can also be deposited over the exposed battery structures (e.g., anode, electrolyte, cathode) in sufficient thicknesses (e.g., 3 μm or greater) to ensure pinhole-free seals protecting the battery structures from exposure to surrounding air.

In medical devices it is often desirable to include a backup power source, such as a second battery, in the event that the first battery fails. The second battery can serve as a total replacement for the first (so that it continues to power all functions) or it can exist merely to provide enough power to properly shut the device down, alert the user, or perform some other critical function in the event of a failure of the main power source. LiPON batteries, for example, are well suited to this task, at least because of their stackable nature. In one embodiment, the battery is actually two (or more) battery elements stacked on top of each other. The capacity of the backup battery can match that of the main battery, or it can store only a fraction of the energy stored in the main battery (e.g., 20% of the main battery's capacity). Circuitry incorporated in the electronics sub-assembly of the implantable device, or even within the battery sub-assembly itself, can detect failure (such as a short circuit or depleted power) and switch to the backup battery if necessary.

One embodiment of the invention may include a power supply including a rechargeable battery, such as, but not limited to, a rechargeable LiPON battery. This may be highly desirable in an implanted device, as it obviates or at least defers the need for additional surgical procedures for changing batteries, etc. In one embodiment, recharging is accomplished through utilization of an RF-coupled wireless power link and, for example, a near-field (e.g., inductively coupled) link, typically employing coils in the transmitter and receiver, or a far-field link, which may employ antennas in the receiver and coil. The frequency of operation can be chosen to suit the application; higher frequencies (e.g., 10 MHz) typically facilitate use of smaller electronic components, as well as enabling greater tissue penetration and higher efficiencies in power coupling, while lower frequencies (e.g., 400 kHz) typically offer lower power consumption and less potential tissue heating due to absorption.

In one embodiment, the substrate on which the battery is deposited also includes recharging circuitry such as, but not limited to, a coil and a capacitor connected to form a resonant circuit for inductive coupling, a rectification stage that converts the resulting alternating current (AC) to direct current (DC) and filters the resulting DC (e.g., through a low-pass filter stage) and a voltage-regulation stage that maintains the proper charging voltage regardless of external influences (movement of the coil, etc.) during the charging process. These components may be discrete or can be fabricated using well-known semiconductor techniques during the same overall manufacturing process that creates the battery layers.

In another embodiment, recharging capability is accomplished using a photovoltaic cell on the same substrate as the LiPON battery. For implants that are close to the surface of the skin, (e.g., an intraocular application whereby the pump is surgically implanted just below the conjunctiva of the eye, an intracranial application whereby the pump is surgically implanted just below the skull, or a neurosurgical application whereby the pump is implanted along the nerve root), energy can be coupled to the device via the photovoltaic cell and a light source, e.g., a laser focused on the location of the implant.

Suitable electronics may provide control and monitoring capabilities as well as any additional required functions for the device. In one exemplary embodiment, the electronics control the pumping mechanism and measure the amount of drug administered. The complexity of the electronics depends on the required functionality, but may include highly complex and integrated functionality that can be packaged in small forms. In one embodiment, the electronics includes off-the-shelf components such as, but not limited to, microcontrollers, op-amps, transistors, resistors, and/or capacitors enclosed in small packages. These components may be mounted on a printed circuit board that provides electrical interconnectivity. In one embodiment, this printed circuit board is of the flex circuit variety (on a polyimide, e.g., KAPTON substrate) to minimize thickness and also provide flexibility so the electronics can match the curvature of the shell (which is itself designed to match the curvature of the eye, knee or brain).

In one embodiment, to minimize size and dimension, the components are packaged together in a system-on-chip (SoC) configuration, e.g., using chip-scale packaging or wafer/die-level and wirebond assembly. In another embodiment, the electronics functions may be custom-designed in an application-specific integrated circuit (ASIC).

The electronics may be coated with a thin conformal coating (such as, but not limited to, epoxy or parylene) to prevent the possibility of a short circuit in the case of a conductive outer shell. Alternatively, the inside of the conductive shell may be coated to prevent shorting. The electronics may also be potted in epoxy either with the shell, or the epoxy potting may serve as the shell itself. The electronics may be housed (e.g., in die or wafer form) in a parylene structure forming a portion of the pump system. The electronics may be wirebonded together, or connective traces may be integrated into the parylene.

In one embodiment, implantable pumps may include means of communicating with, and/or charging, the pump after implantation into a body. This may be advantageous, for example, where hardwired connections to a supply power and/or data communication functionality is impractical for an implanted device. As a result, embodiments of the present invention may utilize a wireless telemetry configuration, whereby power and data are transferred to and from the implant using electromagnetic radiation through means including, but not limited to, an RF link. In such embodiments, the microelectronic implantable device may be coupled to an external device (a "reader/charger"). This external device may provide functions such as, but not limited to, a power supply, battery recharging, and/or forward and reverse telemetry. For example, for devices that do not incorporate internal energy-storage capabilities (i.e., battery or capacitor), the external device can be used to provide power when in proximity to the implanted device, while for devices that incorporate an internal battery or other energy-storage device, the external device can be used to recharge the energy-storage device. The external device can also be used to transmit data to the implanted device and/or receive data sent by the implanted device. This data may include, but is not limited to, pump performance data, drug storage information, and/or medical readings. These functions may be integrated into a single external device, or may be divided among multiple devices. For example, one device may provide power and recharging capabilities while a different device may provide data telemetry functionality.

In one embodiment, the reader/charger (which may be a single device or multiple devices) is controlled by a microcontroller, microprocessor, FPGA, or other digital logic device as well as ancillary circuitry (e.g., random access memory, power regulation, etc.) to enable program storage and otherwise allow the processor to perform its function, and a power source such as rechargeable batteries or a transformer and regulator to facilitate connection to line voltage (110 VAC/220 VAC). The reader/charger may also incorporate non-volatile memory such as flash memory to store data of various types. The reader/charger may have USB or other interface capabilities to allow for data download, firmware updates, etc. In addition, the reader/charger may also incorporate a user interface, with a display (e.g., an LCD) that shows information, and buttons or a keypad enabling the user or clinician to interact with the reader/charger (and, thereby, the implanted device). In addition, the reader/charger includes a coil or antenna and driver circuitry including a power-amplification stage (e.g., class-C or class-E) specifically designed to couple to resonant circuitry (i.e., a coil and capacitor tuned to the resonant frequency) in the implantable device. The coil/antenna may be located within the same enclosure that houses the other components, or it may be external to the enclosure, for example, to facilitate charging and data transfer.

In one example, the implantable device is an intraocular drug pump configured for surgical implantation below the conjunctiva on the eye or brain. In this embodiment, the coil/antenna may be separate from the rest of the reader/charger and installed in a pair of eyeglasses, an eye patch for the eye, a headband for the brain, a kneebrace for the knee, or even a hat, and connected to the main reader/charger circuitry by a cable (or, in some cases, wirelessly). Desirably, the coil is strategically located in a wearable appliance such that, with the appliance properly and naturally positioned on a user, optimal alignment between the implant coil and the reader/charger coil is enforced. This maximizes energy transfer and therefore minimizes recharge time. In an eyeglass configuration, for example, the frame, when worn, will have a consistent alignment with the anatomy that does not vary substantially across wearers. This configuration enables the patient to wear the eyeglasses comfortably during the recharging cycle (which, depending on multiple factors, may take tens of minutes to a few hours). The bulk of the reader/charger can be located elsewhere, such as, but not limited to, in a unit that may be clipped to a patient's belt.

In one embodiment, the implantable device can communicate with a reader/charger including an audiovisual component, such as, but not limited to, a pair of "video glasses" or virtual-reality goggles. The eyeglasses may, if desired, have integrated LCD displays similar to virtual-reality goggles or the "video glasses" currently being sold to interface to audiovisual devices such as iPods. These glasses are capable of displaying video images. The patient can comfortably watch a movie or television show, for example, or an informative or educational video relevant to his or her treatment. The display can also be designed to display information regarding the charge/data telemetry cycle, such as time elapsed/remaining, percent charged, etc.

In addition, the displays may be offset relative to the patient's line of sight so that the patient is forced to view the display at an angle, for example by turning his or her eyes toward the left or the right. This can be useful in achieving optimal coupling to an implant on one of the patient's eyes (e.g., so that the coupling occurs through air, which causes lower attenuation of the signal power than coupling through the flesh and bone near the temple).

In one embodiment, implantable pump systems in accordance with the invention may include a power and/or data telemetry system. For example, a power telemetry system can convert received AC signals transmitted by the external device coil into a DC voltage, which can power the pump and/or recharge the pump's internal power supply. Power transmission is unidirectional and may be accomplished by wirelessly coupling power from an external coil to an internal coil integrated with the pump device packaging. In one embodiment, the internal coil includes or consists essentially of a single or multiple strands (e.g., Litz) of wire with polymer insulation thermally formed by heat treatment into a specific shape. In particular, the coil can be shaped to conform to an anatomical surface, e.g., the eye, to which the pump is attached. In another embodiment, the coil is fabricated through the deposition and etching of a conductive film (e.g., of gold or silver). In yet another embodiment, the coil is fabricated through a lithographic process. More generally, the coil may be fabricated according to any approach convenient to the overall manufacturing process; numerous alternatives (e.g., using Litz wire) are well-known in the art. In an exemplary embodiment, an implantable gold coil, having a diameter of 1 cm, can achieve >100 mW coupling power using a portable, wearable, external coil.

A data telemetry link may use the same set of coils as the power telemetry link, or may use a separate coil. In addition, the implanted coil can serve as both the transmit and the receive coil. The data telemetry functionality can be used, for example, to program device parameters before or after implantation, verify proper programming and functionality, and download status alerts, dosing schedules, and other relevant information stored by the pump (e.g., in non-volatile memory). In various embodiments, antennas and/or coils may be located inside or integrated within a shell material for a pump system (in the case of non-attenuating materials such as polypropylene) or on the outside (in the case of metals and other shielding materials). Depending on the location of the device, it is also possible to locate the coil or antenna a distance from the device enclosure, e.g., a deeply implanted device with a coil located close to the skin surface. In one embodiment, a telemetry/recharging coil may be integrated into a parylene structure forming a portion of the pump system.

If the application does not require power telemetry or data telemetry after implantation, an implantable pump in accordance with the invention can also incorporate a simple and inexpensive unidirectional, optical data-telemetry system (typically requiring fewer components, and less cost and space, than a radio frequency or inductive telemetry link) utilizing, for example, a photodiode or phototransistor. In one embodiment, an external device transmits light signals (for example via a laser or LED) that have been modulated with data; these signals are detected by the photodiode or phototransistor and interpreted by the pump-borne microcontroller or other control circuitry. In one embodiment, the phototransistor and device electronics are located in an enclosure made from a material such as, but not limited to, polypropylene, that is transparent to the wavelength of the optical signals. In another embodiment, the electronics and phototransistor are located in an opaque (e.g., titanium) enclosure containing a transparent (e.g., sapphire) window hermetically sealed (e.g., through a brazing or welding process). One benefit of this sapphire window is to allow an LED light source, attached to and controlled by the electronics, inside the enclosure to signal the patient or another use of some type of message, such as an error light or low battery signal. Other indicators in addition to light include vibration, audible signals, or shock (such as transcutaneous neural stimulation).

A variety of modulation techniques and error detection/correction methods may be implemented. In an exemplary embodiment, the optical telemetry is used to program pump settings (e.g., the current date and time, the desired flow rate, dosing schedule, etc.) immediately prior to implantation, without removing the device from its package (assuming the packaging material is penetrable by the wavelength of the particular light source).

The optical communication can be made bidirectional (thereby enabling the pump to transmit data as well) by adding a light-emitting diode (LED) to the pump circuitry. The LED can emit in the infrared or visible spectrum; for example, an indicator LED may be used for communication functions in addition to display. The bidirectional communication enables the pump to communicate with an external device, for example, to verify proper programming and settings before implantation. The LED may also be used as a photodiode either in photovoltaic mode or photocurrent mode, thereby saving cost and space by using a single component for both transmit and receive functions.

In one embodiment, the control circuitry described herein may be used to detect electrical failures and, for example, switch to a backup battery, if necessary. More generally, the control circuit can be configured to detect any number of failure conditions and to take appropriate ameliorative action. For example, if a malfunction or fault state in the pumping mechanism is detected, the control circuitry may trigger an alert to the patient. The alert may take the form of an optical signal (from the LED described above, for example, which will be immediately visible in ocular deployments); vibration; transcutaneous electric neurostimulation (e.g. giving an electrical shock to the eye); or an audible signal. In one embodiment, the alert may include one or more lights blinking from an LED on the surface of the pump to alert patient in mirror, or LED on an undersurface of a pump to alert the patient's eye through endoillumination. Alerts may be used to notify a patient of events such as, but not limited to, malfunction, low battery, low drug. The control circuitry may communicate details of the failure condition to the wireless reader when it is brought into proximity. Other alerts such as audible signals (e.g. beeping), noises, vibration, and electrical shock may also be used in addition to. Or instead of, an optical signal, as described above.

B. Methods of Manufacture

In one embodiment of the invention, an implantable drug-delivery pump, or components thereof, may be manufactured using techniques including, but not limited to, bonding (e.g., thermal bonding), lithographic etching, and/or other suitable manufacturing techniques. Exemplary techniques for manufacturing various components of the pumps described herein are described below. It should be noted that the methods of manufacture described below are presented as representative examples, and any of the pumps and/or components thereof may be formed using any of the manufacturing methods described, as appropriate, or other suitable methods.

B.1 Method of Manufacturing Top Layer of Drug Chamber and Cannula

An exemplary method of manufacturing a drug chamber 130 with integrated cannula 120 for a pump 100 using lithographic fabrication processes is shown in FIGS. 25A-25F. In this embodiment, a pump 100 having a drug chamber 130, electrolysis chamber 140, and integrated cannula 120 is formed from a plurality of patterned parylene layers. The fabrication process flow includes the steps of:

(a) Spin-coating a thin photoresist layer (e.g., 1 µm) onto a silicon substrate as a sacrificial layer for releasing the finished device from the substrate.

(b) Depositing a first parylene layer (having a thickness, for example, of approximately 20 µm). This layer forms the top of the drug chamber and delivery cannula.

(c) Spin-coating a thick photoresist layer (having a thickness, for example, of approximately 20 µm) as a sacrificial layer that defines the interior dimensions of the drug chamber 130 and the cannula 120. Lithographic patterning by differential exposure may be used to create corrugations in the photoresist surface (e.g., with a 10 µm pitch).

(d) Depositing a second parylene layer (having a thickness, for example, of approximately 20 µm), which forms the bottom and the side of the drug chambers and delivery cannula 120.

(e) Patterning the parylene layers in an RIE oxygen plasma using a thick photoresist layer as a mask.

(f) Removing the sacrificial photoresist layers by subjection to a photoresist stripper such as, but not limited to, acetone. This allows the device to be removed from the silicon substrate.

In one embodiment, by forming components of the pump 100 from a flexible, biocompatible material such as, but not limited to parylene, the drug chamber 130 and cannula 120 are both appropriate form implantation within a body for safe extended use. Similarly, multiple parylene layers can be processed to make other layers of a pump 100, such as, but not limited to a bottom layer of an electrolysis chamber 140.

In one embodiment, a pump 100 may be manufactured by separately forming the discrete layers of the pump 100 (e.g., an upper surface of a drug chamber 130 with integrated cannula 120, a diaphragm 150 dividing the drug chamber 130 and electrolysis chamber 140, and/or a bottom later of an electrolysis chamber 140), and thereafter bonding these layers together through, e.g., thermal and/or chemical bonding.

Figure 26:
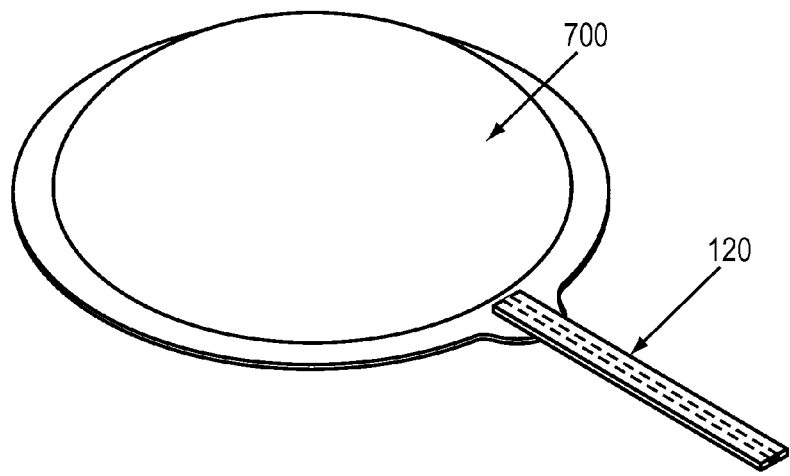
FIG. 26 shows a perspective view of a top layer of a drug chamber with integrated cannula as formed using the process of FIGS. 25A-25F.
Figure 27:
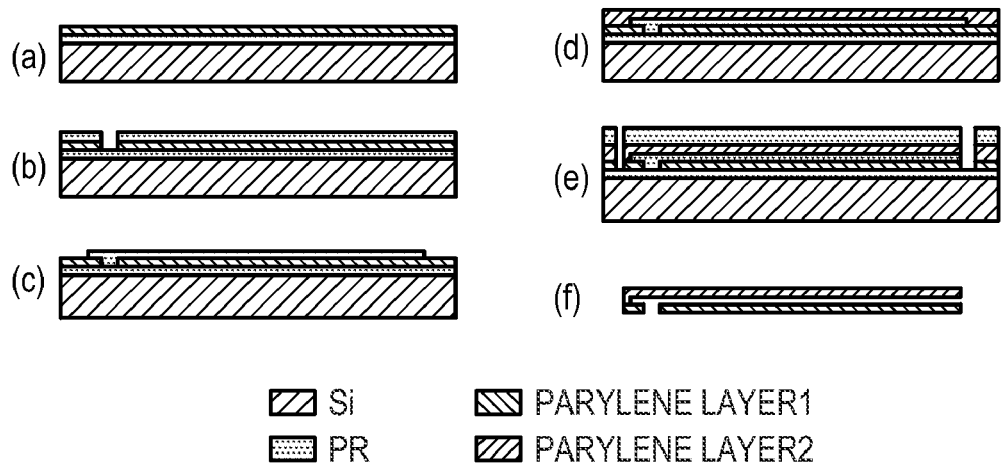
FIG. 27A-27F show steps in the fabrication of another top layer of a drug chamber in accordance with an embodiment of the invention.

A top layer 700 of a drug chamber 130 including an integrated cannula 120 (as shown in FIG. 26) may be manufactured through methods including, but not limited to, molding and/or lithographic etching techniques. An exemplary method of forming a top layer 700 is described below. The top layer 700 may have dimensions such as, but not limited to, 9 mm in diameter and 4 mm in height, with a 9 mm cannula 120 with a micro-channel (9 mm in length, 150 µm in width and 20 µm in height).

In one embodiment, the top layer 700 is formed by coating a layer of material, such as, but not limited to, parylene, of a predetermined thickness onto a mold (e.g., a metal mold formed, for example, from aluminum). After the parylene coating has set, the resulting parylene dome structure may simply be peeled off of the mechanical mold. A cannula 120 may thereafter be inserted into, and/or bonded onto, the parylene structure through a preformed hole. The preformed hole in the top layer 700 may be formed after molding the top layer, for example by piercing the top layer 700 with a sharp object, or may be formed during the molding process itself (with the hole feature created by the mold.

In one embodiment, a top layer 700 is fabricated using a CNC machined mold. Here, a release layer is applied to the mold using spray, dip, and/or other coating methods. Parylene is then deposited on the mold. Afterwards, the molds are soaked in a solution that will dissolve the release layer.

In another embodiment, the top layer 700 is formed by placing a sheet of material (e.g., parylene) between opposing mating surface of a preformed mold. The opposing mating surfaces may be formed from a metal (e.g., aluminum), a plastic, rubber, or another material exhibiting the required strength, thermal properties, and chemical stability. The parylene dome structure for the top layer 700 is then made by pressing a flat parylene sheet between the mold portions, and annealed in a vacuum oven (e.g., at a temperature such as, but not limited to, under 180° C. to 200° C.), after which the mold may be separated and the completed part removed.

B.2 Method of Forming and Integrating Cannula using Epoxy Bonding

A parylene cannula 120 incorporating a micro-channel may be fabricated by a lithography process using two parylene layers, as shown in FIGS. 27A-27F. The steps include:

(a) Spin-coating a thin photoresist layer (e.g., 1 µm) onto a silicon substrate as a sacrificial layer for releasing the finished device from the substrate. The first parylene layer (having a thickness, for example, of approximately 10 µm) is then deposited thereon. This layer forms the bottom of the delivery cannula.

(b) Etching a through-hole (having a diameter, for example, of approximately 140 µm) through the first parylene layer. Reactive-ion etching (RIE) plasma may be used to etch the parylene and a thick photoresist is used as the etching mask.

(c) Spin-coating a thick photoresist (having a thickness, for example, of approximately 20 µm) as a sacrificial layer that defines the interior dimensions of the channel;

(d) Depositing a second parylene layer (having a thickness, for example, of approximately 10 µm) on the photoresist. This layer forms the top and the side of the delivery cannula.

(e) Patterning the parylene layers in a RIE oxygen plasma using thick photoresist as a mask.

(f) Removing the sacrificial photoresist layers by subjection to photoresist stripper. This allows the device to be removed from the silicon substrate.

Figure 28:
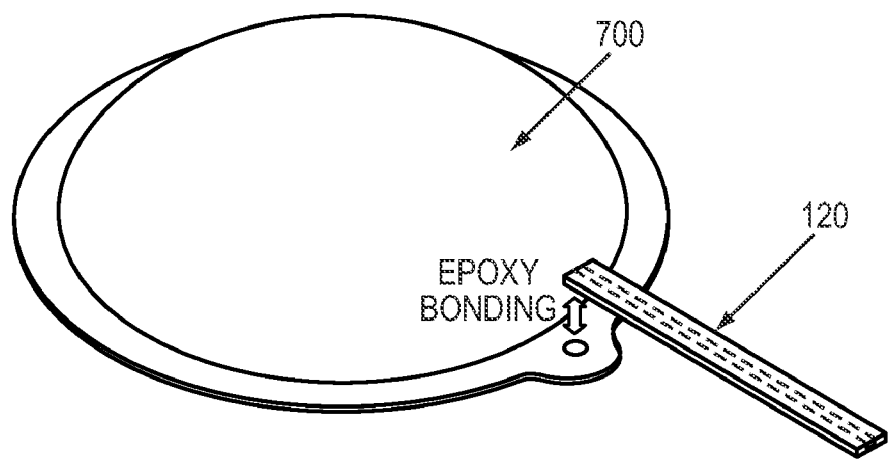
FIG. 28 shows a perspective view of a cannula being integrated with a top layer of a drug chamber using the process of FIGS. 27A-27F.
Figure 29:
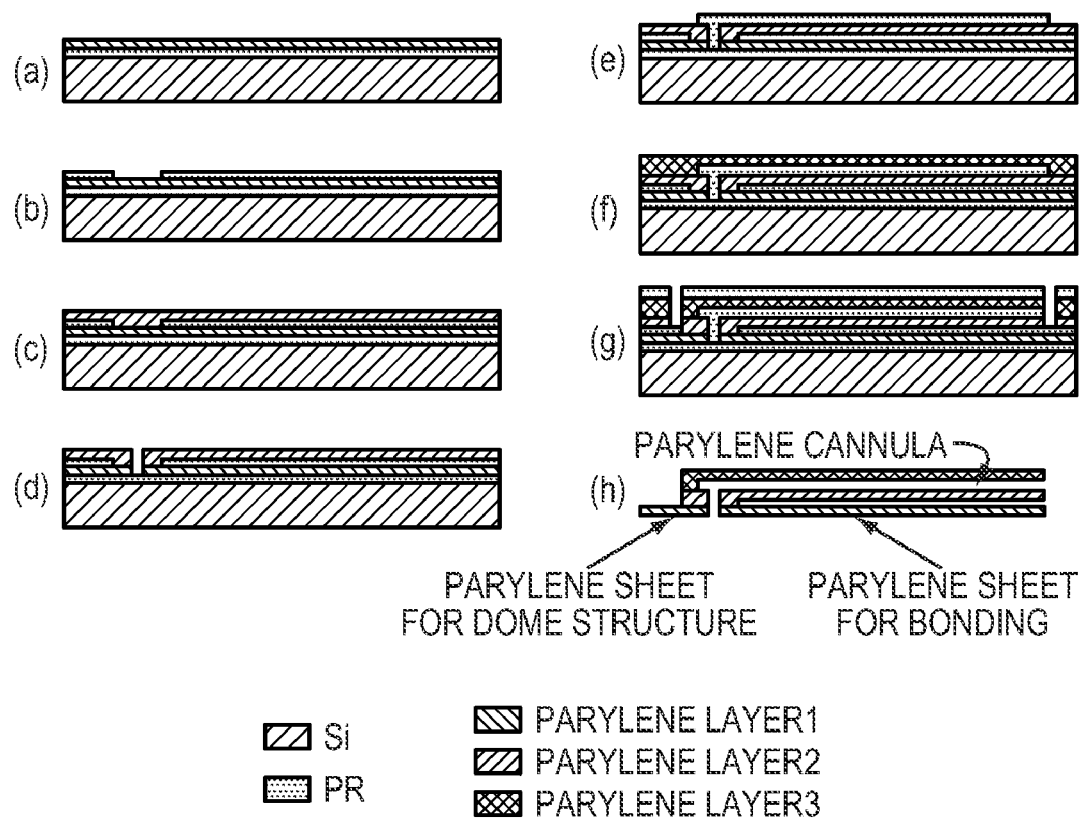
FIGS. 29A-29H show steps in the fabrication of another top layer of a drug chamber with integrated cannula in accordance with an embodiment of the invention.

After forming the cannula, a parylene dome structure 730 may be bonded to the cannula 120, as shown in FIG. 28. A through-hole is created, e.g., with a hot metal probe, at the edge of the dome 730 and the parylene cannula 120 is bonded to the parylene dome 730, e.g., using a biocompatible epoxy, while ensuring the through holes in the dome structure and the parylene cannula are properly aligned.

B.3 Method of Forming and Integrating Cannula using Lithography

In one exemplary embodiment, as shown in FIGS. 29A-29H, a cannula 120 and top layer of a drug chamber 130 may be formed using a lithography process. Besides two parylene layers for the cannula and its micro-channel, another parylene layer (e.g., 20 μm in thickness), which is used for making the dome structure (by thermal molding following basic fabrication) and bonding area under the cannula, is incorporated within the fabrication process. Compared with the epoxy bonding method described above, this method integrates the parylene cannula 120 and the dome structure using lithography. As a result, the alignment and epoxy bonding work is not needed. By avoiding possible misalignment or epoxy failure (e.g., blockage of the micro-channel or leakage via the epoxy bonding), the lithography fabrication method may increase the reliability of the device. The steps include:

(a) Spin-coating a thin photoresist layer (e.g., 1 μm) onto a silicon substrate as a sacrificial layer for releasing the finished device from the substrate. The first parylene layer (having a thickness, for example, of approximately 20 μm) is deposited. This layer forms the flat parylene sheet for making the dome structure using the thermal molding process and the parylene sheet for bonding under the cannula.

(b) Spin-coating another thin photoresist layer (e.g., 1 μm) onto the first parylene layer and an area for adhesion to the parylene cannula 120 is opened by lithography.

(c) The second parylene layer (having a thickness, for example, of approximately 10 μm) is then deposited to form the bottom of the cannula 120.

(d) A hole through the first and the second parylene layers is etched by RIE oxygen plasma and masked by thick photoresist.

(e) A thick photoresist (having a thickness, for example, of approximately 20 μm) for the sacrificial layer of the channel is spin-coated and patterned.

(f) The third parylene layer (having a thickness, for example, of approximately 10 μm) is coated to form the top and the sides of the parylene channel.

(g) The parylene channel is patterned by etching through the third and the second parylene layers. The etching process is stopped before reaching the first parylene layer.

(h) All photoresist layers are removed by soaking in photoresist stripper.

B.4 Method of Manufacturing Cannula Integrated with Check Valve and Flow Sensor One manufacturing method includes a lithography process to integrate a check valve 200 and flow sensor 205 inside a parylene micro-channel cannula 120. The check valve 200 is used to prevent drug leakage from the drug chamber when the pump 100 is at rest and during the refilling. The check valve 200 also prevents back-flow due to intraocular pressure after implantation, such as during a patient's sneeze or pressurization on an airplane. An exemplary check valve 200 is a bandpass check valve.

Figure 30:
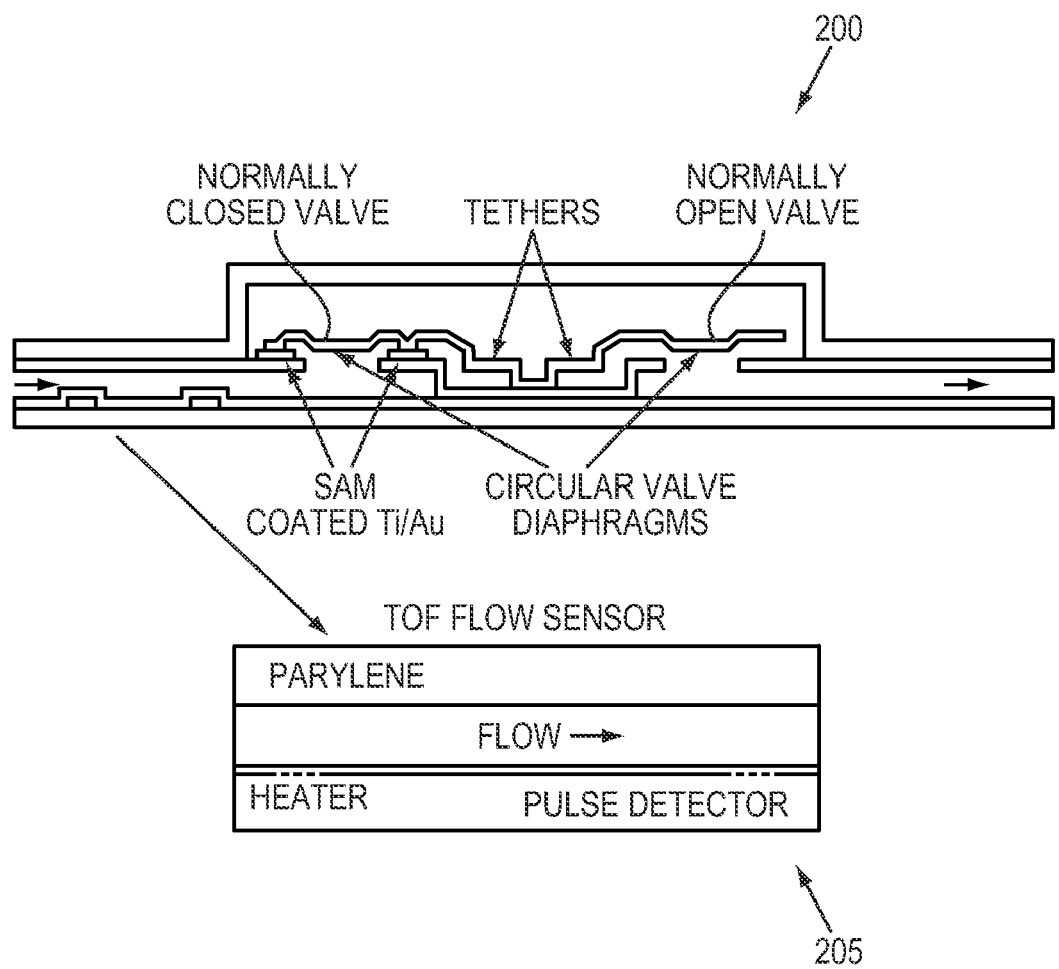
FIG. 30 shows a perspective sectional view a check valve in accordance with one embodiment of the invention.
Figure 31:
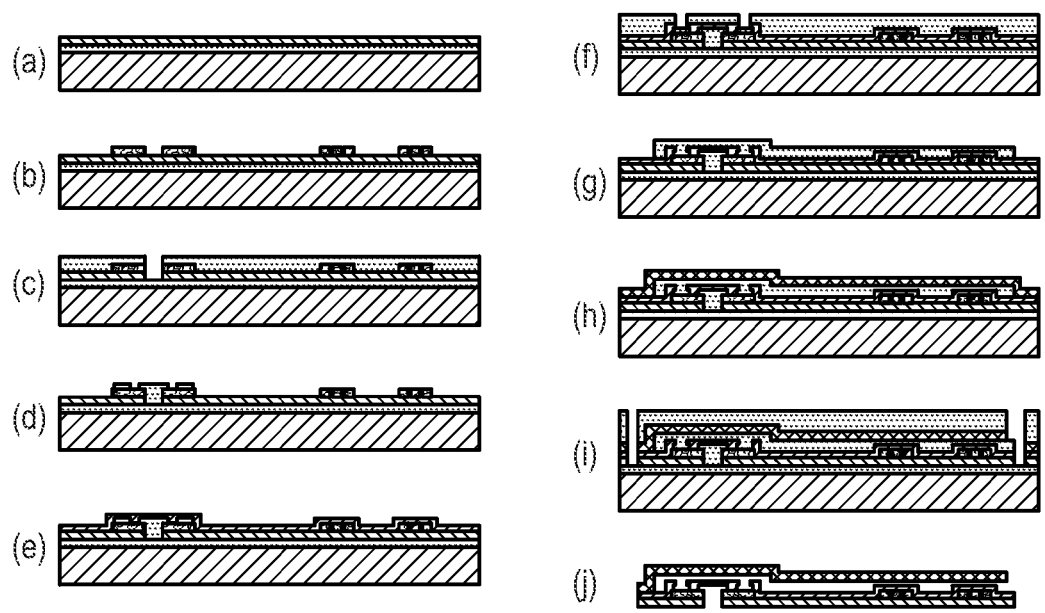
FIGS. 31A-31J show steps in the fabrication of a cannula with integrated check valve and sensor in accordance with an embodiment of the invention.

The check valve's cracking pressure prevents leakage when the pump is at rest (and during the refill process), but the valve will open to allow forward flow when the electrolysis pumping action is working normally to generate a pressure exceeding the cracking pressure. However, when the drug chamber 130 experiences an extremely high (i.e., abnormal) pressure, due, for example, to drug refilling, unexpected force on drug chamber 130 during operation of implantation, etc., the check valve 200 will shut down the forward the flow. In addition, the check valve 200 will prevent backward flow resulting from the intraocular pressure. In one embodiment, a bandpass check valve may be manufactured by combining one normally closed and one normally open check valve, as shown in FIG. 30.

A thermal, time-of-flight, capacitive or other type of flow sensor 205 may be used in the micro-channel cannula 120. The flow sensor 205 may be on upstream or downstream of the check valve to monitor the drug pumping rate and/or the total volume. In one embodiment, the flow sensor includes two parts: a heater on the upstream side to generate a heat pulse in the flow, and a thermal sensor or other type of sensor to sense and pick up the pulse. By monitoring the exact time between application of the heat pulse and its detection by the sensor the flow rate may be precisely established and, using a microcontroller, a total volume of pumped drug may be calculated.

An exemplary process for manufacturing a micro-channel cannula 120 with integrated check valve 200 and flow sensor 205 is shown in FIGS. 31A-31J. The manufacturing steps include:

(a) Spin-coating a thin photoresist layer (e.g., 1 μm) onto a silicon substrate as a sacrificial layer for releasing the finished device from the substrate. The first parylene layer (having a thickness, for example, of approximately 10 μm) is deposited. This layer forms the flat parylene sheet for making the dome structure using a thermal molding process and the parylene sheet for bonding under the cannula.

(b) A Cr/Au, Ti/Au, or Pt (100 Å/2000 Å) layer is evaporated, and a lift-off or wet etching process is used to pattern the metal layer for the check valve ring. Another thin metal layer (e.g., 500 Å of Au or Pt) is deposited and patterned for the flow sensor 205.

(c) A "via" is etched through the first parylene layer by RIE oxygen plasma etching using photoresist as etching mask.

(d) A photoresist sacrificial layer (having a thickness, for example, of approximately 10 μm) is coated and patterned for the check valve 200 chamber.

(e) The second parylene layer (having a thickness, for example, of approximately 5 μm) is coated for moving diaphragm of the check valve 200 and the protective layer for the flow sensor 205.

(f) The tethers of the check valve 200 are patterned by RIE oxygen plasma etching using photoresist as etching mask.

(g) The second photoresist sacrificial layer (having a thickness, for example, of approximately 20 μm) is coated and patterned for the check valve 200 chamber and the micro-channel.

(h) The third parylene layer (having a thickness, for example, of approximately 10 μm) is coated to form the top and the sides of the parylene cannula channel.

(i) The parylene channel is patterned by etching through all the three parylene layers.

(j) All photoresist layers are removed by soaking in photoresist stripper.

Figure 32A:
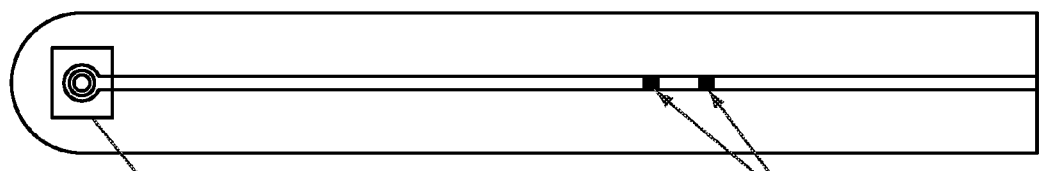
FIG. 32A shows a schematic plan view of a cannula incorporating a check valve and flow sensors.
Figure 32B:
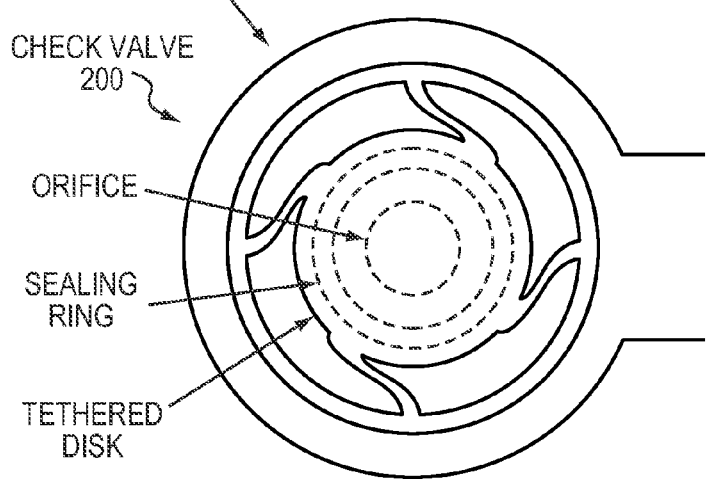
FIG. 32B is an enlarged schematic plan view of the check valve shown in FIG. 32A.
Figure 32C:
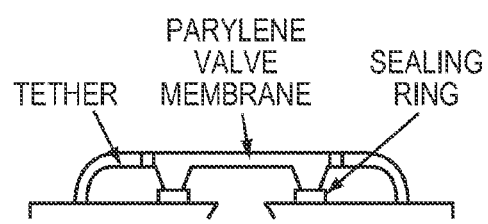
FIG. 32C is a front sectional view of the check valve shown in FIG. 32B.
Figure 33:
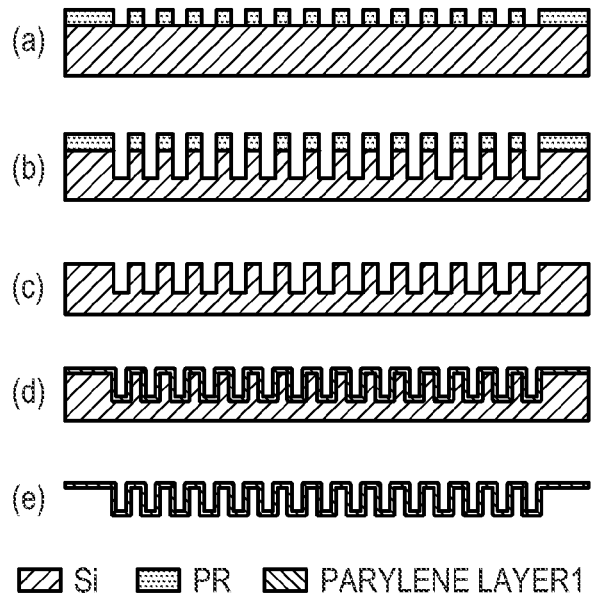
FIGS. 33A-33E show steps in the fabrication of a middle diaphragm layer of a pump having corrugations in accordance with an embodiment of the invention.
Figure 34:
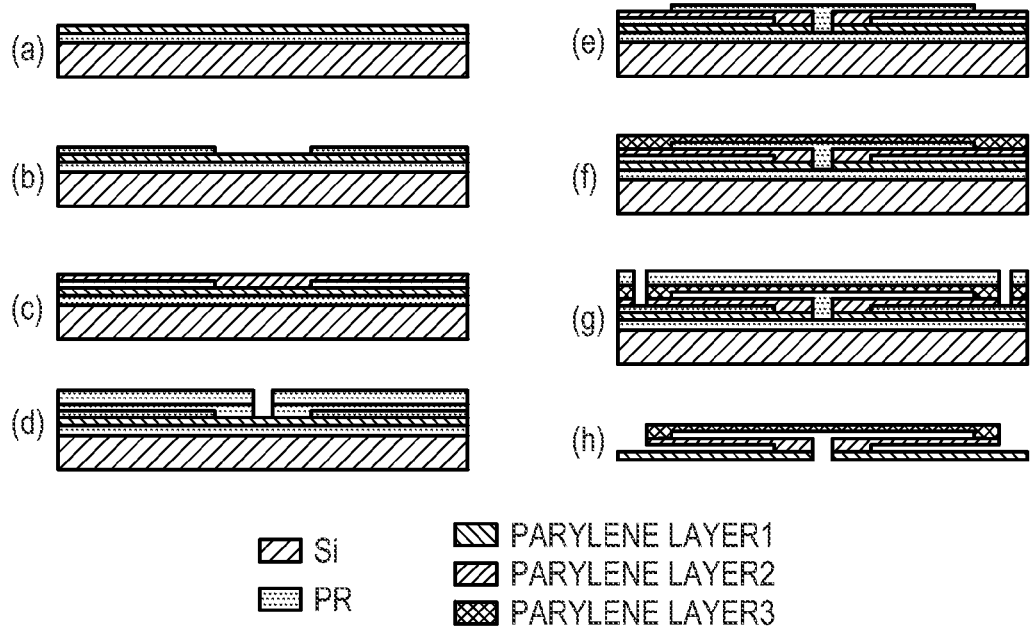
FIGS. 34A-34H show steps in the fabrication of a middle diaphragm layer of a pump having bellows folds in accordance with an embodiment of the invention.
Figure 35:
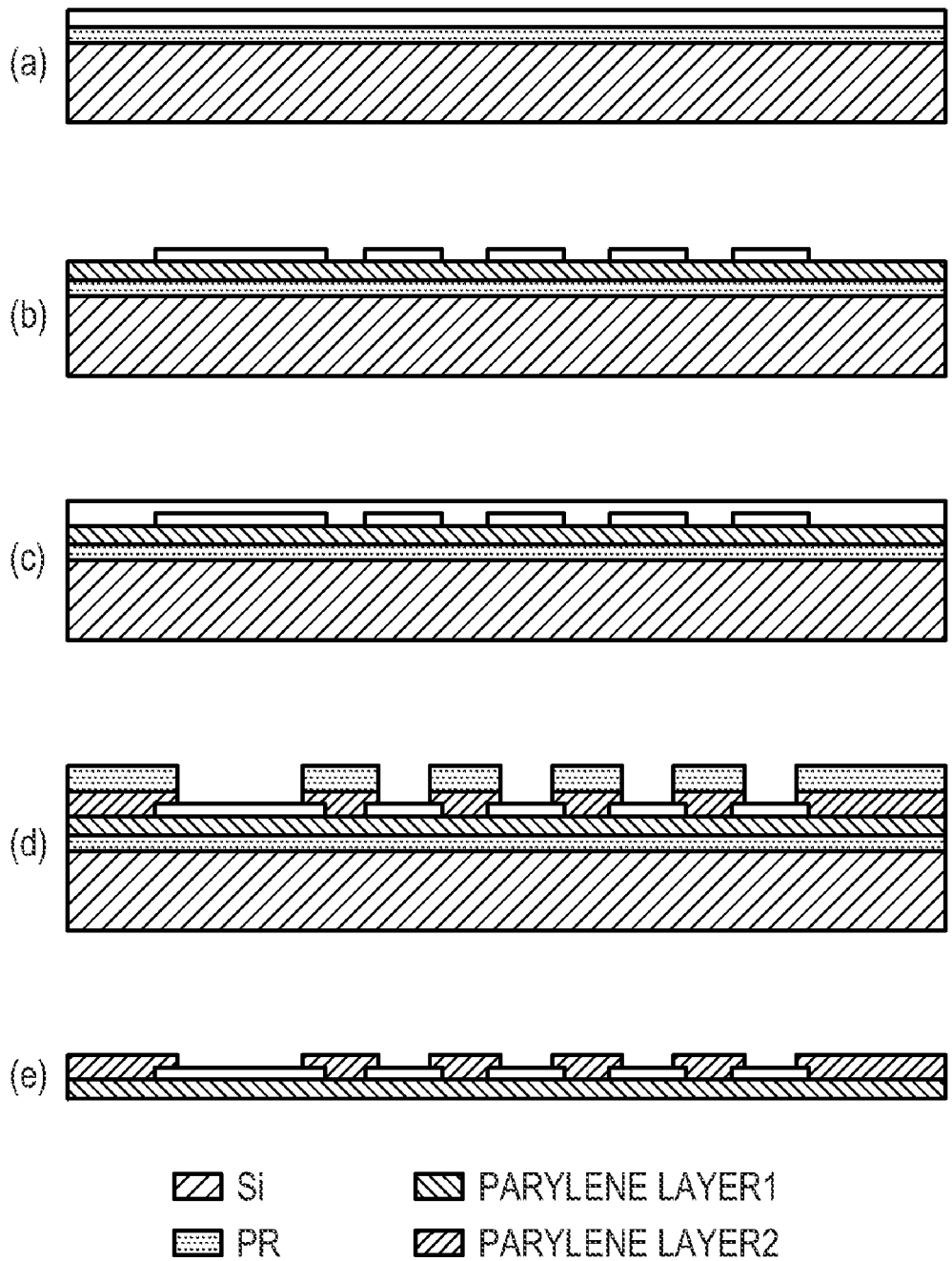
FIGS. 35A-35E show steps in the fabrication of a bottom layer of a drug chamber including electrolysis electrodes in accordance with an embodiment of the invention.
Figure 36:
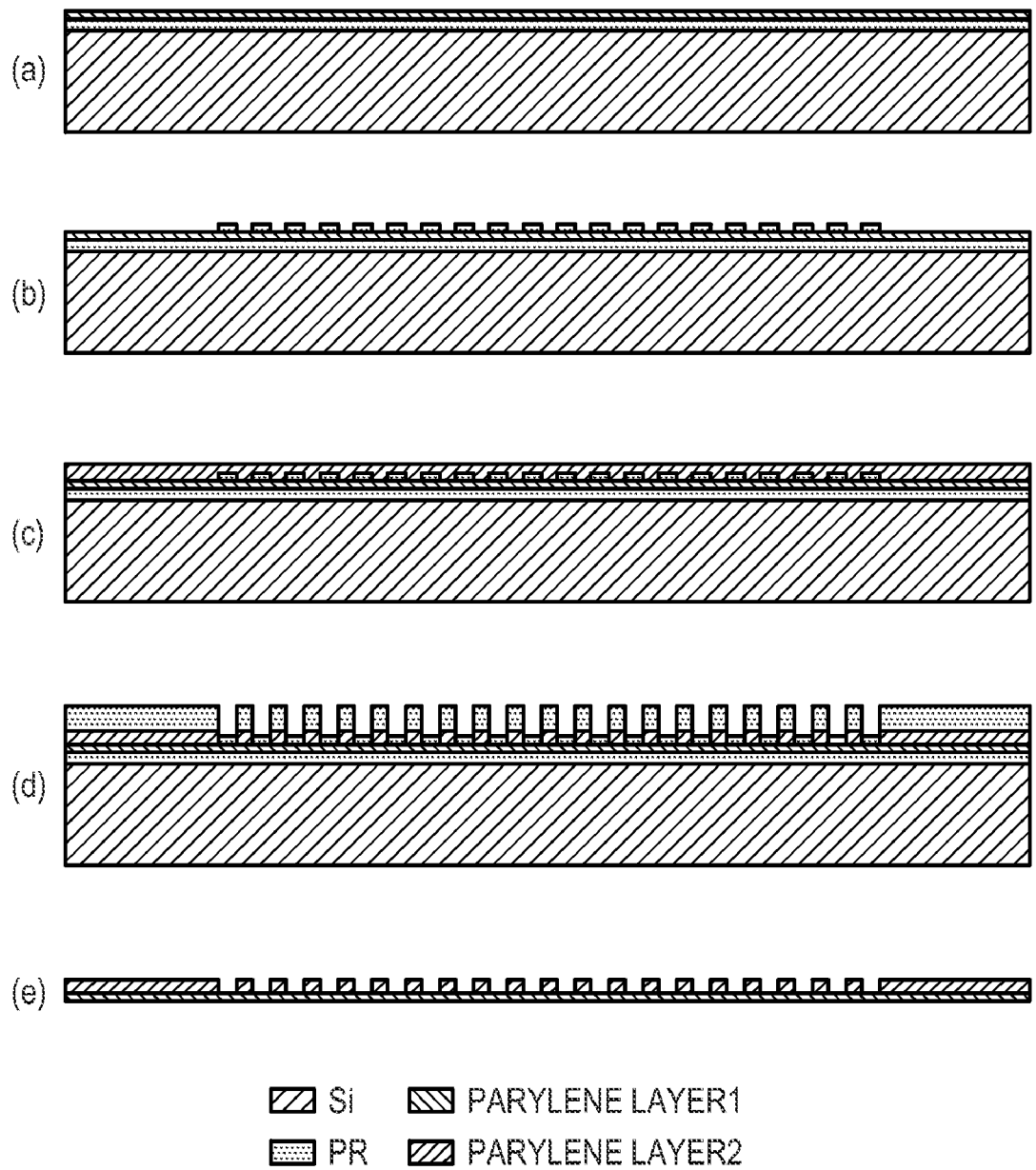
FIGS. 36A-36E show steps in the fabrication of an osmosis chamber for a pump in accordance with an embodiment of the invention.

A cannula 200 resulting from use of the foregoing method, and including a check valve 200 and flow sensor 205, is shown in FIG. 32.

B.5 Method of Manufacturing a Middle Deflection Layer Diaphragm with Corrugations In one embodiment, a diaphragm 150 with corrugations may be formed by coating a layer of material such as, but not limited to, parylene, over a mold. Alternatively, diaphragm 150 with corrugations may be formed by placing a parylene sheet between two complementary mold portions, and annealing the mold and sheet at a set temperature to form the required structure.

In an alternative embodiment, a diaphragm 150 with corrugations may be formed by a lithographic process, as shown in FIGS. 33A-33E. The manufacturing steps include:

(a) Spin-coating and patterning a thick photoresist layer (e.g., 60 µm) onto a silicon substrate.

(b) Using a deep RIE (Bosch process) to etch silicon (e.g., in 100 µm to 200 µm deep channels), using a photoresist layer as mask.

(c) Removing the photoresist layer by soaking in photoresist stripper. A photoresist release layer is applied on the silicon trench structure by spray coating.

(d) Coating a parylene layer with certain thickness (e.g., 10 µm) on the silicon mold.

(e) Releasing the parylene layer by soaking in photoresist stripper.

B.6 Method of Manufacturing a Middle Deflection Layer Diaphragm with Bellows

In one embodiment, a diaphragm 150 with bellows may be formed by coating a layer of material such as, but not limited to, parylene, over a mold. Alternatively, diaphragm 150 with bellows may be formed by placing a parylene sheet between two complementary mold portions, and annealing the mold and sheet at a set temperature to form the required structure.

In one embodiment, a diaphragm 150 with bellows may be formed by a lithographic process, as shown in FIGS. 34A-34H. The manufacturing steps include:

(a) Spin-coating a thin photoresist layer (e.g., 1 µm) onto a silicon substrate as a sacrificial layer for releasing the finished device from the substrate. The first parylene layer (having a thickness, for example, of approximately 10 µm) is deposited. This layer forms the bellows' first layer.

(b) Another thin photoresist layer (e.g., 1 µm) is spin-coated onto the first parylene layer and an area for adhesion to the second parylene layer is opened by lithography.

(c) The second parylene layer (having a thickness, for example, of approximately 10 µm) is then deposited to form the bellows' second layer.

(d) A hole through the first and the second parylene layers is etched using RIE oxygen plasma and masked by thick photoresist.

(e) A thick photoresist (having a thickness, for example, of approximately 20 µm) for the sacrificial layer of the channel is spin-coated and patterned.

(f) The third parylene layer (having a thickness, for example, of approximately 10 µm) is coated to form the bellows' third layer.

(g) The bellows' leaf is patterned by etching through the third and the second parylene layers. The etching process is stopped before reach the first parylene layer.

(h) All photoresist layers are removed by soaking in photoresist stripper.

B.7 Method of Manufacturing a Bottom Layer of a Pump including Electrolysis Electrodes In one embodiment, a bottom layer of an electrolysis chamber 140 within electrolysis electrodes 240 attached thereto may be formed by a lithographic process, as shown in FIGS. 35A-35E. In one embodiment, the electrolysis electrode 240 is a sandwich structure with a platinum layer between two parylene layers. The platinum layer is deposited and patterned on a parylene substrate layer (having a thickness, for example, of approximately 20 µm), and a top parylene layer is coated and patterned to open the center area of the platinum electrode, forming a protective layer for the electrode during electrolysis. The manufacturing steps include:

(a) Spin-coating a thin photoresist layer (e.g., 1 µm) onto a silicon substrate as a sacrificial layer for releasing the finished device from the substrate. The first parylene layer (typically 20 µm) is deposited.

(b) Depositing a metal (e.g., 0.2 µm platinum) by E-beam evaporation (or other appropriate deposition method) and patterned by a conventional lift-off process or etching process.

(c) The second parylene layer (having a thickness, for example, of approximately 10 µm) is then deposited.

(d) The second parylene layer is etched by RIE oxygen plasma and masked by thick photoresist to open the electrodes area.

(e) All photoresist layers are removed by soaking in photoresist stripper. An annealing process (e.g., 200° C. in vacuum oven) is then performed to improve the adhesion between the parylene and platinum layers.

B.8 Method of Manufacturing an Osmosis Chamber having a Permeable Membrane

In one embodiment, an osmosis chamber for a pump 100 may be manufactured through lithography-based fabrication. The permeable portion may be formed, for example, by using parylene layers; areas with multiple layers of parylene are substantially impermeable, whereas areas with a single layer of parylene are permeable or semi-permeable. A film layer may be domed to create the saline chamber. Alternatively, a membrane may be made from a flat film of parylene and subsequently attached to a base layer. The manufacturing steps, as shown in FIGS. 36A-36E, include:

(a) Spin-coating a thin photoresist layer (e.g., 1 µm) onto a silicon substrate as a sacrificial layer for releasing the finished device from the substrate. The first parylene layer (typically less than 1 µm) is then deposited thereon. This layer forms the thin permeable parylene areas.

(b) Spin-coating and patterning a second photoresist layer (e.g., 4 µm). This layer forms the etch stop layer for the second parylene layer.

(c) Depositing a second parylene layer (e.g., 20 µm).

(d) The second parylene layer is patterned by RIE oxygen plasma etching, using photoresist layer as etching mask. Etching is monitored and stopped after reach the photoresist etching stop layer under the second parylene layer.

(e) All the photoresist layers are removed by subjection to photoresist stripper. This allows the device to be removed from the silicon substrate.

B.9 Method of Manufacturing an Electrolysis Chamber

In one embodiment, an electrolysis chamber 140 may be formed by thermally bonding the edges of a parylene film with platinum electrodes with a corrugated parylene diaphragm 150. The diaphragm 150 may have a step (e.g., 0.4 mm high) on the edge so that when it is placed upside down, the recess can be filled with electrolyte and the edges then thermally bonded (through, for example, local heating only) to seal the electrolyte inside the chamber. An exemplary process for manufacturing a parylene film with platinum electrodes is shown in FIG. 37. In a first step, a thin photoresist layer (e.g., 1 µm) is spin-coated onto a silicon substrate as a sacrificial layer for releasing the finished device from the substrate. A parylene layer is then deposited thereon, and a platinum layer is deposited over the parylene layer. The platinum layer is patterned by etching. A second parylene layer is deposited over the patterned platinum, and this layer is itself patterned by etching. Finally, the photoresist layer is removed by subjection to photoresist stripper, and the backside of the revealed parylene layer is etched to open contact regions using a shadow mask. Annealing is performed at, e.g., 200° C. in a vacuum oven for 10 hours.

In some embodiments, there are two backside contacts on the film so that the electrical leads do not pass through the bonding edge (which may, for example, make them vulnerable to damage from the thermal-bonding process). Therefore, in embodiments having at least 10 µm of parylene everywhere on the film to minimize liquid permeation, the total parylene thickness in most areas will be approximately 20 µm. The electrolysis electrode material may be pure platinum with no adhesion layer (because a typical adhesion layer would generally not survive electrolysis). The adhesion between platinum as deposited and parylene is sufficient to survive the fabrication process. However, even with another parylene layer coated to cover the side and patterned to expose the top surface partially, electrolysis might still delaminate the platinum and parylene in as little as 10 min. One approach to solving this problem is to anneal the finished film at 200° C. in a vacuum oven for 10 hours.

B.10 Method of Manufacturing a Corrugated Diaphragm

One embodiment of a pump utilizes a circular diaphragm 10 mm in diameter with corrugations 100 µm deep and 100 µm wide. The peak vertical displacement is 2 mm under a differential pressure of 1.2 psi. Increasing the parylene thickness decreases liquid permeation about linearly, but will stiffen the diaphragm. It may be helpful to blocking permeation that a thin layer of platinum is deposited on electrolysis side. This platinum also assists gas recombination following electrolysis. However, platinum cannot be stretched as much as parylene. An exemplary process for manufacturing a corrugated diaphragm 150 is shown in FIG. 38. A bare silicon wafer is patterned using deep reactive ion etching. A photoresist (e.g., SU-8) layer is selectively applied to the patterned silicon wafer outside the area of patterning in order to elevate the profile, and a thin layer of photoresist is then spray-coated over the entire structure. A layer of parylene (e.g., 10 µm) is applied over the photoresist. If necessary, platinum may be applied using a shadow mask to cover areas outside the corrugations. The resulting parylene diaphragm may then be cut and released.

In an alternative embodiment, corrugations may be formed by photopatering a thick photoresist layer on a silicon wafer. The parylene is then deposited directly on the photoresist. Once again, the diaphragms can be coated with platinum if necessary. The diaphragms are then cut and released, as before. As a result, photoresist is used to create the mold features instead of ion etched silicon. The use of photoresist as the mold structure also negates the need to spray a thing photoresist release layer prior to Parylene deposition.

B.11 Method of Manufacturing a Drug Reservoir

A drug reservoir 130 may be formed by bonding a parylene-coated hard shell to the edge of the parylene film with platinum electrodes, e.g., using laser bonding. Since the bonding temperature may exceed 290° C., one suitable material for the shell may include, or consist essentially of, a ceramic. A refill port, formed, for example, from NU-SIL silicone, may be integrated with the shell.

A drug reservoir 130 may also be manufactured where the dome structure is manufactured by providing a mold having a domed shape, conformably coating a layer of material on the mold, and after the material has set, peeling the resulting dome structure from the mold. Alternatively, the dome structure may be manufactured according to steps including providing a first mold element having a domed shape, providing a second complementary mold element, conformably disposing a sheet of material between the first mold element and the second complementary mold element, heating the first mold element, the second complementary mold element, and the conformed sheet of material to anneal the sheet of material, and removing the first mold element and second complementary mold element from the annealed sheet of material.

B.12 Alternative Method of Manufacturing a Cannula with Integrated Check Valve and Flow Sensor In one embodiment, a cannula 120 may be formed as long parylene channel (having dimensions, for example, of 10 µm high, 100 µm wide and over 1 cm long) with a normally closed check valve 200 near the entrance and a time-of-flight flow sensor 205 somewhere in the middle. An exemplary process for manufacturing the cannula 120, similar to the process illustrated in FIGS. 31A-31J, is shown in FIG. 39.

A thin photoresist layer (e.g., 1 µm) is applied to a silicon substrate as a sacrificial layer for releasing the finished device from the substrate. The first parylene layer is then deposited. A layer of platinum is deposited and patterned, and a second layer of parylene coated thereon. A layer of Ti/Au is then deposited and patterned. The parylene layers are patterned to open the inlet to the valve, and a self-assembled monolayer (SAM) is applied thereon. Two successive steps of coating and patterning a photoresist layer, followed by depositing a parylene layer thereon, are then performed. All photoresist layers are removed by soaking in photoresist stripper and the cannula thereby released. The backside contacts are opened using a shadow mask.

The design may be modified slightly by adding another parylene layer, as shown in FIG. 40. In this embodiment, the inlet is horizontal and can have a long length. After testing, the inlet can be cut before the check valve 200 and the device are re-used.

The pump 100, or components thereof, may be configured to allow for semi-automated volume production. For example, a jig assembly may be used to align the multiple parylene layers and facilitate thermal bonding. In an embodiment that automates the pump filling process, the parylene chambers are aligned with each other, with small spouts (e.g., hypodermic tubing) inserted into each chamber during the alignment process and before thermal bonding occurs. The parylene layers are then thermally bonded, electrolyte and drug are dispensed via the spouts into their respective chambers, the spouts are retracted and the fill holes are then thermally sealed.

In another embodiment, a refill port is aligned with the three parylene layers prior to thermal bonding and is permanently attached to the drug and/or electrolysis chambers during the bonding process. The electrolyte and drug chambers may be filled during the bonding process, as described above, or afterwards via the refill port. The multiple parylene layers of the pump, including, for example, the top parylene layer with dome structure and cannula, the middle deflection layer with corrugation or bellows, and the bottom parylene layer with electrolysis electrodes, may be bonded together to seal the drug chamber and electrolysis chamber at the same time using thermal bonding.

C. Sterilization of Drug-Delivery Pump Components

One embodiment of the invention includes methods of sterilizing a drug-delivery pump, or components thereof. Sterilization techniques may used to sterilize any of the pumps, or components, described herein. For example, sterilization may include a two-step sterilization process with gamma radiation on just the parylene structure followed by sterilizing gas exposure on the entire assembled device.

An exemplary sterilization technique includes the sterilization of a drug-delivery pump having at least two sealed chambers, i.e., an electrolysis chamber filed with a working fluid and a drug reservoir filled with a drug. The pump may also have a sealed enclosure containing electrical components for control and/or monitoring of the pump. The membranes that form at least one wall of at least one of the sealed chambers may, for example, be corrugated parylene diaphragms.

In an exemplary embodiment, the sterilization technique sterilizes a pump in a manner that does not damage heat-sensitive components. This may be achieved, for example, by subjecting portions of the pump to radiational sterilization (e.g., exposure to E-beam radiation or gamma radiation) and/or exposing the pump to a sterilizing gas such as, but not limited to, ethylene oxide (EtO).

Sterilization of a pump, in accordance with this embodiment of the invention, may include the following steps. Firstly, one or more membranes used to construct the chambers of the pump are subjected to radiational sterilization or to a sterilizing gas. The sterilized membranes are then attached to the sealed enclosure to form the sealed chambers thereover.

The sealed chambers themselves are then sterilized, for example, by introducing a sterilizing gas (e.g., EtO) through their respective refill ports. As the chambers are devoid of contents following assembly, there is no gas or liquid to displace, and the sterilizing gas fills the chambers to their working volumes. However, if this is not the case, the chambers can first be subjected to negative pressure through their refill ports to create a vacuum therein, after which the sterilizing gas may be introduced. After sterilization of each chamber, the chambers are filled with their respective working liquids (e.g., a drug, a electrolysis fluid, etc).

Before or after the chambers are filled with their working liquids, the entire structure (including, for example, the sealed enclosure and sealed chambers, and also including any reservoir wall mounted over the drug-reservoir membrane) is subjected to a sterilization technique, such as exposure to a sterilizing gas that does not harm heat-sensitive components. The device may now be hermetically packaged in sterilized form.

In other embodiments, sterilization techniques may include additional or different methods of sterilizing components of the pumps, and/or include additional or differently ordered sterilization processes, depending on the particular pump construction and use.

Figure 41:
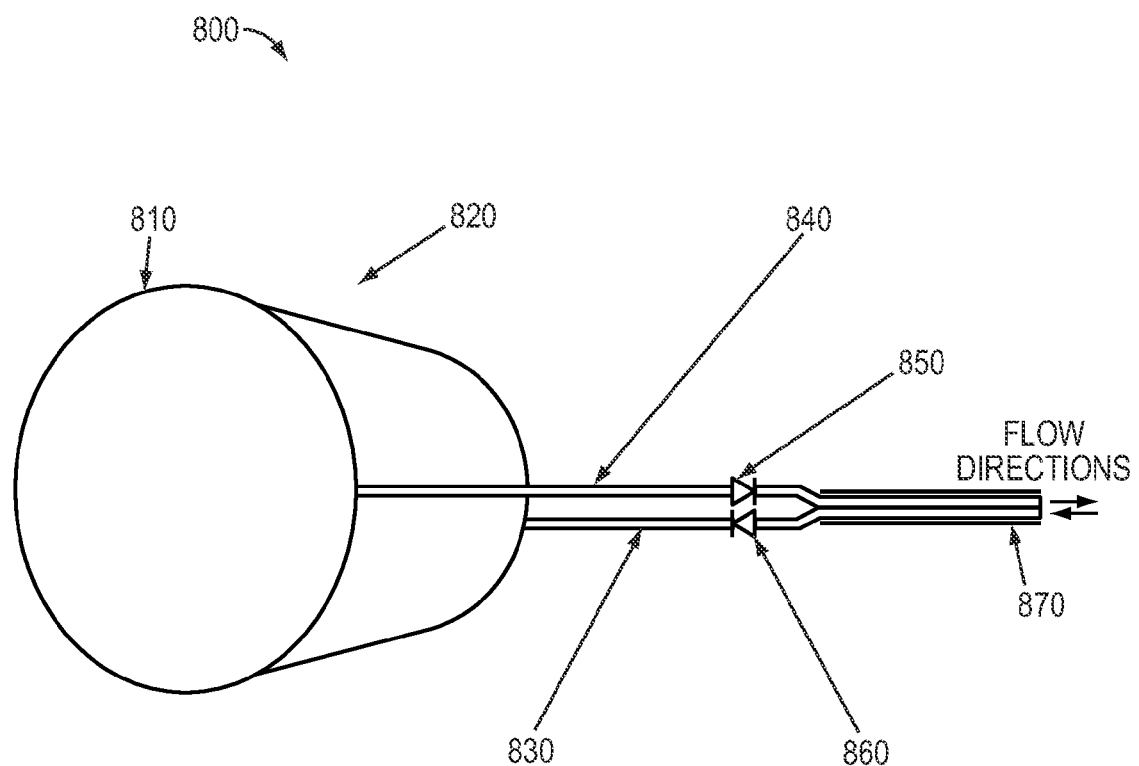
FIG. 41 is a schematic plan view of a glaucoma drainage device with integrated drug pump, in accordance with one embodiment of the invention.

One embodiment of the invention includes the incorporation of the drug delivery pumps described herein into medical treatment devices such as, but not limited to, a glaucoma drainage device. An example glaucoma drainage device 800 including a pump 810 is shown in FIG. 41. In this embodiment, the drug pump 810 is coupled to a glaucoma drainage device end plate 820 and simultaneously acts to dissipate aqueous fluid. Two parallel cannulas 830, 840 extend from the drug pump 810/end plate 820 structure, with one cannula 830 serving as a pathway for aqueous outflow from the eye to the end plate 820, and the other cannula 840 serving as a pathway for the drug to be delivered into the anterior chamber from the pump 810. Check valves 850, 860 are located with the cannulas 830, 840 to control the fluid flow therethrough. The check valve 850 in the drug delivery pump cannula 840 only allows liquid flowing from the drug chamber of the pump 810 into the target treatment site within the eye. A separate cannula 830 (with a reverse check valve 860) is also in fluid communication with the target treatment site but opens up when Intraocular Pressure (IOP) rises above a certain amount such as 17 mm HG (in early to mid stage Glaucoma) and 12 mm HG (for late stage glaucoma). This allows fluid to flow back through the cannula 830 into the glaucoma drainage device 800 when the pressure exceeds the set limit. The two cannulas 830, 840 may be assembled into a single cannula sleeve 870, thereby requiring only one cut to insert the cannulas 830, 840 during implantation.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An implantable electrolytic pump comprising:
    a first expandable diaphragm and a second flexible diaphragm;
    first and second chambers each for containing a fluid, wherein the first expandable diaphragm separates the first and second chambers and provides a fluid barrier therebetween, and the second chamber is formed between the first expandable diaphragm and the second flexible diaphragm;
    a perforated shell over the second flexible diaphragm;
    a cannula for conducting liquid from the second chamber; and
    electrolysis electrodes within the first chamber for causing generation of a gas therein and to thereby expand the expandable diaphragm so that fluid is forced from the second chamber into the cannula, whereby body fluid is admitted through the shell perforations to relieve vacuum pressure on the second chamber.

2. The pump of claim 1, wherein the perforated shell is substantially rigid.

3. The pump of claim 1, wherein the perforated shell comprises or consists essentially of at least one of a biocompatible plastic material or a metal.

4. The pump of claim 1, further comprising a casing.

5. The pump of claim 4, wherein the perforated shell forms part of the casing.

6. The pump of claim 4, wherein the casing comprises or consists essentially of a material selected from the group consisting of a ceramic, an epoxy encapsulation, a metal, polyetheretherketone (PEEK), polypropylene, polydimethylsiloxane (PDMS), and parylene.

7. The pump of claim 6, wherein the metal comprises or consists essentially of titanium, niobium, or nitinol.

8. The pump of claim 4, wherein the casing is at least partially coated with parylene.

9. The pump of claim 1, wherein the perforated shell has a thickness of greater than 0.1 mm.

10. The pump of claim 1, wherein the perforated shell comprises a plurality of perforations for allowing a body fluid to flow therethrough.

11. The pump of claim 10, wherein the perforations are sized and shaped to allow a body fluid to flow therethrough at a sufficient rate to substantially offset a vacuum pressure applied to the second flexible diaphragm.

12. The pump of claim 1, further comprising at least one refill port.

13. The pump of claim 1, wherein the diaphragms comprise or consist essentially of parylene or a composite material.

14. The pump of claim 13, wherein the composite material is platinum and parylene.

15. The pump of claim 1, further comprising circuitry, disposed below the first chamber and electrically connected to the electrodes, for operating the electrodes.

16. The pump of claim 15, wherein the circuitry adjustably controls a flow rate from the second chamber.

17. The pump of claim 15, wherein the circuitry comprises at least one of a data storage means, a data transmission means, or a data receiving means.

18. The pump of claim 17, wherein the data transmission means comprises a wireless telemetry circuit.

19. The pump of claim 17, wherein the circuitry is secured to the electrodes by a conductive epoxy.

20. The pump of claim 19, wherein the conductive epoxy comprises or consists essentially of a biocompatible material.

21. The pump of claim 20, wherein the biocompatible material comprises or consists essentially of gold or silver.

22. The pump of claim 15, wherein the circuitry provides an adjustable current or voltage to the electrolysis electrodes to adjustably control a flow rate from the second chamber.

23. The pump of claim 1, wherein the electrolysis electrodes comprise or consist essentially of at least one of platinum, gold, or silver on parylene, ceramic, or a biocompatible insulator.

24. The pump of claim 1, wherein at least one of the expandable membranes comprises corrugations.

25. The pump of claim 1, wherein at least one of the expandable membranes comprises perimeter bellows folds.

26. The pump of claim 1, wherein the first chamber contains at least one fluid that evolves gas upon activation of the electrolysis electrodes.

27. The pump of claim 26, wherein the gas returns to a liquid state upon deactivation of the electrolysis electrodes.

28. The pump of claim 26, wherein the at least one fluid comprises a saline solution, a solution comprising magnesium sulfate, a solution comprising sodium sulfate, or pure water.

29. The pump of claim 1, wherein the first chamber comprises a recombination catalyst.

30. The pump of claim 29, wherein the recombination catalyst comprises platinum.

31. The pump of claim 1, further comprising an osmotic diaphragm between the second flexible diaphragm and the perforated shell.

32. The pump of claim 31, wherein a third chamber is formed between the second flexible diaphragm and the osmotic diaphragm.

33. The pump of claim 32, wherein the osmotic diaphragm is at least partially anchored to the perforated shell.

34. The pump of claim 32, further comprising at least one osmosis chamber fluid within the third chamber.

35. The pump of claim 34, wherein the at least one osmosis chamber fluid comprises at least one solvent and at least one solute.

36. The pump of claim 34, wherein the fluid comprises a saline solution, a solution comprising magnesium sulfate, or a solution comprising sodium sulfate.

37. The pump of claim 32, further comprising a refill port in fluid communication with the third chamber.

38. The pump of claim 32, wherein the osmotic diaphragm allows a surrounding body fluid to flow into the third chamber at a sufficient rate to substantially offset a pressure applied to the second flexible diaphragm.

39. The pump of claim 1, wherein the perforated shell comprises an osmotic diaphragm.

40. The pump of claim 1, further comprising at least one of a check valve, a pressure sensor, or a flow sensor.

41. The pump of claim 40, wherein the at least one a check valve, pressure sensor, or flow sensor is located within the cannula.

42. The pump of claim 40, wherein the check valve prevents leakage of a fluid from the second chamber when the pump is at rest or during a refilling process.

43. The pump of claim 40, wherein the check valve prevents backward fluid flow through the cannula and into the second chamber.

44. The pump of claim 1, comprising a plurality of first chambers.

45. The pump of claim 44, comprising a plurality of second chambers above the plurality of first chambers.

46. The pump of claim 45, wherein each second chamber comprises a refill port.

47. The pump of claim 45, further comprising at least one cannula in fluid communication with each of the plurality of second chambers.

48. The pump of claim 44, further comprising separately controllable electrolysis electrodes within each of the plurality of first chambers.

49. The pump of claim 1, further comprising a plurality of cannulas in fluid communication with the second chamber.

50. The pump of claim 46, wherein each cannula comprises at least one of a check valve or sensor.

* * * * *